US009023806B2

(12) United States Patent
Bocquet et al.

(10) Patent No.: US 9,023,806 B2
(45) Date of Patent: May 5, 2015

(54) PEPTIDE CAPABLE OF ALTERING TUBULIN POLYMERIZATION AND USE THEREOF FOR INHIBITING CELL PROLIFERATION

(75) Inventors: Arnaud Bocquet, Castres (FR); Joël Eyer, Blaison-Gohier (FR); Alan Peterson, Westmount (CA)

(73) Assignees: Universite d'Angers, Angers (FR); Institut National de la Sante et de la Recherche Medicale (Inserm), Paris (FR); McGill University, Montreal (CA)

( * ) Notice: Subject to any disclaimer, the term of this patent is extended or adjusted under 35 U.S.C. 154(b) by 1933 days.

(21) Appl. No.: 11/579,548

(22) PCT Filed: Apr. 21, 2005

(86) PCT No.: PCT/FR2005/000990
§ 371 (c)(1),
(2), (4) Date: Jan. 9, 2008

(87) PCT Pub. No.: WO2005/121172
PCT Pub. Date: Dec. 22, 2005

(65) Prior Publication Data
US 2009/0221476 A1    Sep. 3, 2009

(30) Foreign Application Priority Data
May 4, 2004    (FR) ..................... 04 04742

(51) Int. Cl.
A61K 38/16    (2006.01)
A61K 38/10    (2006.01)
G01N 33/53    (2006.01)
C12N 5/00     (2006.01)
A61K 38/00    (2006.01)
C07K 14/47    (2006.01)

(52) U.S. Cl.
CPC ................... C07K 14/4703 (2013.01)

(58) Field of Classification Search
None
See application file for complete search history.

(56) References Cited

U.S. PATENT DOCUMENTS 5,958,684 A * 9/1999 Van Leeuwen et al. ..... 435/6.14
2004/0058326 A1 * 3/2004 Brooksbank et al. ........... 435/6
2013/0004429 A1  1/2013 Eyer et al.

FOREIGN PATENT DOCUMENTS

EP    1 284 298      * 2/2003  ............... C12Q 1/68
WO    WO9845322      * 10/1998 ............. C07K 14/00
WO    WO 03/057168 A2  7/2003

OTHER PUBLICATIONS

Nakahira et al. 1990. J. Biol Chem. 265:19786-19791.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Bocquet et al. 2009. J Neurosci. 29:11043-11054.*
Hisanaga et al. 1991. J. Biol. Chem 266:21798-21803.*
Database EMBL Aug. 1, 1988, XP00208298 Extraits de EBI Database accession No. P08551, 2 pages.
Lewis et al., "Anomalous Placement of Introns in a Member of the Intermediate Filament Multigene Family: an Evolutionary Conundrum," Molecular and Cellular Biology, May 1986, 6(5)1 529-1534, XP002308295.
Database Geneseq Online Nov. 20, 2003, "Alzheimer's disease-associated protein isoform tryptic peptide #618," XP002308299, Extraits de EBI accession No. GSN:ADA24009 Database accession No. ADA24009, 1 page.
Database Uniprot Online, Oct. 1, 1989, "Neurofilament triplet M protein (160 kDa neurofilament protein) (Neurofilament medium polypeptide) (NF-M)," XP002308300 extraits de EBI accession No. UNIPROT:NFM_RAT, Database accession No. P12839; Q63370, 2 pages.
Napolitano et al., "Complete Amino Acid Sequence an in vitro Expression of Rat NF-M The Middle Molecular Weight Neurofilament Protein," J. Neuroscience, Aug. 1987, 7(8):2590-2599, XP009040735.
Database EMBL, XP002308301 extrait de EBI, Database accession No. Q80TQ3, 1 page, Mar. 1, 2004.
Okazaki et al. "Prediction of the Coding Sequences of Mouse Homologues of KIAA Gene: II. The Complete Nucleotide Sequences of 400 Mouse KIAA-homologous cDNAs Identified by Screening of Terminal Sequences of cDNA Clones Randomly Sampled from Size-fractionated Libraries," DNA Research, 2003, 10(1):35-48, XP002969478.
Hisanaga et al., "Dephosphorylation-induced Interactions of Neurofilaments with Microtubules," J. Biol. Chem., Dec. 15, 1990, 265(35):21852-21858, XP002308297.
Tamai et al., "Sequence of the Endo A gene encoding mouse cytokeratin and its methylation state in the CpG-rich region," Gene, 1991, 104(2):169-176, XP002353420.
Karpov et al., "Structure of the mouse gene encoding peripherin: a neuronal intermediate filament protein," Biology of the Cell, 1992, 76(1):43-48, XP002353421.
Chien et al., "Characterization of the mouse gene encoding the neuronal intermediate filament protein α-internexin," Gene, 1994, 149(2):289-292, XP002353422.
Balcarek et al., "Structure of the mouse glial fibrillary acidic protein gene: implications for the evolution of the intermediate filament multigene family," Nucleic Acids Research, 1985, 13(15):5527-5543, XP002353423.

(Continued)

Primary Examiner — Shulamith H Shafer
(74) Attorney, Agent, or Firm — Foley & Lardner LLP

(57) ABSTRACT

The invention concerns a peptide derived from intermediate filaments and an intermediate filament fragment capable of altering tubulin polymerization and used for inhibiting cell proliferation, and more particularly for obtaining medicines designed to prevent or treat diseases involving cell proliferation, such as cancers for example.

13 Claims, 24 Drawing Sheets

(56) References Cited

OTHER PUBLICATIONS

Figure 1A:
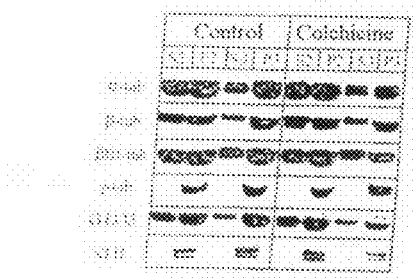

Capetanaki et al., "Mouse vimentin: structural relationship to fos, jun, CREB and tpr," Oncogene, 1990, 5(5):645-655, XP009056912.
Mericskay et al., "An Overlapping CArG/Octamer Element is Required for Regulation of desmin Gene Transcription in Arterial Smooth Muscle Cells," Developmental Biology, 2000, 226(2)192-208, XP002296355.
Strausberg et al., "Generation and initial analysis of more than 15,000 full-length human and mouse cDNA sequences," PNAS, Dec. 24, 2002, 99(26):16899-16903., XP002353426.
Leterrier et al., "Properties of highly viscous gels formed by neurofilaments in vitro, A possible consequence of a specific inter-filament cross-bridging," Biochem. J., 1987, 245:93-101.
Fabrizi et al., "Charcot-Marie-Tooth disease type 2E, a disorder of the cytoskeleton," Brain, 2007, 130:394-403.
Carden et al., "Two-Stage Expression of Neurofilament Polypeptides During Rat Neurogenesis with Early Establishment of Adult Phosphorylation Patterns," The Journal of Neuroscience, Nov. 1987, 7(11):3489-3504.
Cassimeris, Lynne, "The oncoprotein 18/stathmin family of microtubule destabilizers," Curr. Opin. Cell Biol., 2002, 14:18-24.
Chomczynski et al., "Single-step method of RNA isolation by acid guanidinium thiocyanate-phenolchloroform extraction," Anal. Biohcm., 1987, 162:156-159 (Abstract, 1 page).
Chou et al., "The relative roles of specific N- and C-terminal phosphorylation sites in the disassembly of intermediate filament in mitotic BHK-21 cells," Journal of Cell Scinece, 1996, 109:817-826.
Chou et al., "Nestin Promotes the Phosophorylation-dependent Disassembly of Vimentin Intermediate Filaments During Mitosis," Molecular Biology of the Cell, Apr. 2003, 14:1468-1478.
Cory et al., "Use of an aqueous soluble tetrazolium/formazan assay for cell growth assays in culture," Cancer Commun., 1991, 3:207-212 (Abstract, 1 page).
DeWaegh et al., "Local modulation of neurofilament phosphorylation, axonal caliber, and slow axonal transport by myelinating Schwann cells," Cell, 1992, 68:451-463 (Abstract, 1 page).
Eyer et al., "Influence of the phosphorylation state of neurofilament proteins on the interactions between purified filaments in vitro," Biochem. J., 1988, 252:655-660.
Eyer et al., "Neurofilament-deficient axons and perikaryal aggregates in viable transgenic mice expressing a neurofilament-β-galactosidase fusion protein," Neuron, 1994, 12:389-405 (Abstract, 1 page).
Fort et al., "Various rat adult tissues express only one major mRNA species from the glyceraldehyde-3-phosphate-dehydrogenase multigenic family," Nucleic Acids Res., 1985, 13:1431-1442 (Abstract, 1 page).
Frank et al., "SPOT-Synthesis: Epitope analysis with arrays of synthetic peptides prepared on cellulose membranes," Methods in Molecular Biology, 1996, 66:149-169 (Abstract, 1 page).
Goto et al., "Phosphorylation of Vimentin by Rho-associated Kinase at a Unique Amino-terminal Site That is Specifically Phosphorylated during Cytokinesis," J. Biol. Chem., May 8, 1998, 273(19):11728-11736.
Guillaud et al., "Stop Proteins are Responsible for the High Degree of Microtubule Stabilization Observed in Neuronal Cells," J. Cell. Biol., 1998, 142:167-179.
Hirokawa, Nobutaka, "Cross-linker System between Neurofilaments, Microtubules and Membranous Organelles in Frog Axons Revealed by the Quick-freeze, Deep-etching Method," J. Cell. Biol., Jul. 1982, 94:129-142.
Hoffman et al., "Neurofilament and Tubulin Expression Recapitulates the Developmental Program during Axonal Regeneration: Induction of a Specific β-tubulin Isotype," PNAS, 1988, 85:4530-4533.
Hoffman et al., "Neurofilament Gene Expression: A Major Determinant of Axonal Caliber," PNAS, 1987, 84:3472-3476.
Julien et al., "Multiple Phosphorylation Sites in Mammalian Neurofilament Polypeptides," J. Biol. Chem., Sep. 10, 1982, 257(17):10467-10470.
Ku et al., "Phosphorylation of human keratin 18 serine 33 regulates binding to 14-3-3 proteins," the EMBO Journal, 1998, 17(7):1892-1906.
Laemmli, U.K., "Cleavage of Structural Proteins during the Assembly of the Head of Bacteriophage T4," Nature, 1970, 227:680-685, (Abstract, 1 page).
Lee et al., "Identification of the Major Multiphosphorylation Site in Mammalian Neurofilaments," PNAS, 1988, 85:1998-2002.
Mandelkow et al., "Microtubes and microtubule-associated proteins," Curr. Opin. Cell Biol., 1995, 7:72-81.
Ohara et al., "Neurofilament deficiency in quail caused by nonsense mutation in neurofilament-L gene," J. Cell Biol., 1993, 121:387-395 (Abstract, 1 page).
Robert et al., "Neurofilament Cytoskeleton Disruption Does Not Modify Accumulation of Trophic Factor mRNA," J. Neuroscience Research, 2001, 64:487-492.
Toivola et al., "Type II Keratins Are Phosphorylated on a Unique Motif during Stress and Mitosis in Tissues and Cultured Cells," Molecular Biology of the Cell, Jun. 2002, 13:1857-1870.
Weingarten et al., "A Protein Factor Essential for Microtubule Assembly," PNAS, 1975, 72:1858-1862.
Zhu et al., "Delayed Maturation of Regenerating Myelinated Axons in Mice Lacking Neurofilaments," Exp. Neurol., 1997, 148:299-316 (Abstract, 1 page).
Zhu et al., "Disruption of the NF-H Gene Increases Axonal Microtubule Content and Velocity of Neurofilament Transport: Relief of Axonopathy Resulting from the Toxin β,β-Iminodipropionitrile," J. Cell. Biol., 1998, 143:183-193.
Pearson et al., "Improved tools for biological sequence comparison," Proc. Natl. Acad. Sci. USA, vol. 85, pp. 2444-2448, Apr. 1988.
Needleman et al., "A General Method Applicable to the Search for Similarities in the Amino Acid Sequence of Two Proteins," J. Mol. Biol., vol. 48, pp. 443-453, 1970.
Smith et al., "Comparison of Biosequences," Advances in Applied Mathematics, vol. 2, pp. 482-489, 1981.
Betts, M. J. and Russell, R. B. (2003) Amino Acid Properties and Consequences of Substitutions, in Bioinformatics for Geneticists, pp. 298-310 (eds. M. R. Barnes and I. C. Gray), John Wiley & Sons, Ltd. (published online).
Taylor, W.R. et al., "The classification of amino acid conservation," J. Theor. Biol., (1986), pp. 205-218 vol. 119, No. 2.

\* cited by examiner

A

B

Figure 8A   Figure 8A'   Figure 8A"

PEPTIDE CAPABLE OF ALTERING TUBULIN POLYMERIZATION AND USE THEREOF FOR INHIBITING CELL PROLIFERATION

The present invention relates to a peptide derived from intermediate filaments and a fragment of intermediate filament that are capable of altering tubulin polymerization and are used for inhibiting cell proliferation, and more particularly for obtaining medicinal products that are intended for preventing or treating diseases involving cell proliferation, for example cancers.

Cell division, or mitosis, is the process that enables cells to multiply in order to construct or regenerate tissues or to replace dead cells. In cancer cells the regulation of this process is faulty, which is why these cells divide uncontrollably and thus create tumors. One effective therapeutic route for combating cancers comprises blocking the division of cancer cells.

Existing antimitotic molecules (Taxol or colchicine) act on all cells without distinction and consequently give rise to numerous side-effects.

It is therefore essential to develop antimitotic molecules, i.e. molecules that block the division of cancer cells, that have far fewer side-effects.

Tubulin is a fundamental molecule in the process of cell division. In fact, it polymerizes to form the microtubules that are indispensable for intracellular transport during mitosis.

The microtubules constitute one of the most important elements of the axonal cytoskeleton, where they play an essential role in axonal transport, acting as rails along which the organelles move in both directions—anterograde and retrograde—owing to specific driving proteins. The microtubules are in dynamic equilibrium with the tubulin dimers and their assembly is largely controlled by association of additional proteins which enable the stability of the microtubules to be increased or reduced, for example MAPs (reviewed by Mandelkow and Mandelkow, 1995), STOP proteins (Guillaud et al., 1998) and the OP18 proteins (Cassimeris, 2002). The axons depend on the microtubules for axoplasmic transport and on the neurofilaments for their radial growth.

The neurofilaments (NFs) form the major class of intermediate filaments expressed by mature neurons (Hoffman et al., 1987). They are made up of three independently encoded subunits, the light neurofilaments (NFL), the medium neurofilaments (NFM) and the heavy neurofilaments (NFH) of 68, 150 and 200 kDa respectively. The axis of each neurofilament is formed by NFL subunits. The NFM and NFH subunits become fixed on this axis owing to helix-helix types of interactions located in their central domains. The carboxy-terminal domains of NFM and NFH form particularly long lateral projections which permit interfilamentary interactions and the association of neurofilaments with other organelles (Hirokawa, 1982). The state of phosphorylation of the KSP repeat units in these lateral projections (Julien and Mushynski, 1982; De Waegh et al., 1992; Lee et al., 1988) is known to modulate interfilamentary affinity (Eyer and Leterrier, 1988), interfilamentary spacing (Carden et al., 1987), interaction with tubulin (Hisanaga and Hirokawa, 1990), the velocity of transport of the neurofilaments (De Waegh et al., 1992) and the radial growth of the axons (Ohara et al., 1993; Eyer and Peterson, 1994; Zhu et al., 1997).

It is known that the intermediate filaments have the particular feature of being different from one tissue to another. Thus, neurofilaments are only present in neurons, glial filaments in glial cells, desmin filaments in muscle cells, and keratin filaments in the cells of the epidermis.

The inventors demonstrated, surprisingly and unexpectedly, that fragments of intermediate filaments can bind tubulin alter microtubule polymerization. Furthermore, the inventors showed that the use of a peptide that binds tubulin and inhibits or activates polymerization of the microtubules makes it possible to block cell division.

Moreover, said peptides come from the intermediate filament sequence and are tissue-specific. Therefore these peptides do not appear to cause the side-effects of existing antimitotic molecules.

The invention therefore relates to an isolated peptide, characterized in that it has at least 80% and preferably 85%, 90%, 95%, 98% and 100% of identity after optimum alignment with an intermediate filament fragment sequence capable of altering tubulin polymerization.

In particular, the invention relates to an isolated peptide, characterized in that it has at least 80% and preferably 85%, 90%, 95%, 98% and 100% of identity after optimum alignment with particular intermediate filament fragment sequences, the neurofilaments, capable of altering tubulin polymerization.

The invention also relates to an isolated peptide, characterized in that it has at least 80% and preferably 85%, 90%, 95%, 98% and 100% of identity after optimum alignment with a particular intermediate filament fragment sequence, the protein desmin, capable of altering tubulin polymerization.

The invention further relates to an isolated peptide, characterized in that it has at least 80% and preferably 85%, 90%, 95%, 98% and 100% of identity after optimum alignment with a particular intermediate filament fragment sequence, the protein vimentin, capable of altering tubulin polymerization.

The invention further relates to an isolated peptide, characterized in that it has at least 80% and preferably 85%, 90%, 95%, 98% and 100% of identity after optimum alignment with a particular intermediate filament fragment sequence, the protein cytokeratin, capable of altering tubulin polymerization.

The invention further relates to an isolated peptide, characterized in that it has at least 80% and preferably 85%, 90%, 95%, 98% and 100% of identity after optimum alignment with a particular intermediate filament fragment sequence, the protein Glial Fibrillary Acidic Protein (GFAP), capable of altering tubulin polymerization.

"Altering tubulin polymerization" means either inhibiting or activating the polymerization of tubulin.

Thus, one object of the present invention is therefore an isolated peptide, characterized in that it comprises a peptide having at least 80% and preferably 85%, 90%, 95%, 98% and 100% of identity after optimum alignment with a sequence selected from SEQ ID No. 5 (FGYDPYFSTSYKRRYVETPRVHIS), SEQ ID No. 6 (YSSYSAPVSSSLSVRRSYSSSSGS), SEQ ID No. 7 (AYRRVPTETRSSFSRVSGSPSSGFRSQSWSRGSPSTVSS), SEQ ID No. 8 (RSAAGSSSGFHSWARTSVSSVSASPSRFRGAASSTDSLD), SEQ ID No. 17 (MSQAYSSSQRVSSYRRTFGGAPGFSLG), SEQ ID No. 18 (SSPVFPRAGFGTKGSSSSMTSRVYQVSRTSGGAGGLGSLRSSRLGTTRAPSYGA), SEQ ID No. 19 (GSEVHTKKTVMIKTIETRDGE), SEQ ID No. 20 (MSTRSVSSSSYRRMFGGS), SEQ ID No. 21 (GGAYVTRSSAVRLRSSVPGVRLLQ), SEQ ID No. 22 (SLPLVDTHSKRTLLIKTVETR), SEQ ID No. 23 (MSIRVTQKSYKMSTSGPRAFSSRSFTSGPGARISSSSFSRVGSSSSSFRGSMGT), SEQ ID No. 24 (QIKSLNNKFASFIDKVRFLEQ), SEQ ID No. 25 (SAGGSNTFSRTTKAVVVKKIETRDGKLVSE), SEQ ID No. 26 (MERRRITSARRSYASETVVRGLGP), SEQ ID No. 27 (VRGLGPSRQLGTMPRFSLSRMTPPLPARVDFSLAGA), SEQ ID No. 28 (KSVSEGHLKRNIVVKTVEMRD) or one of its biological fragments that is artificial of at least 5 amino acids capable of altering tubulin polymerization.

In the present invention, the term "peptide" is also intended to denote the polypeptides.

In the present invention, the term "peptide" is also intended to denote the oligomeric polypeptides comprising at least 2 repeat sequences selected from SEQ ID No. 5, No. 6, No. 7, No. 8, No. 17, No. 18, No. 19, No. 20, No. 21, No. 22, No. 23, No. 24, No. 25, No. 26, No. 27 and No. 28 and combinations thereof.

In the present invention, the term "peptide" is also intended to denote the oligomeric polypeptides comprising at least 3 repeat sequences selected from SEQ ID No. 5, No. 6, No. 7, No. 8, No. 17, No. 18, No. 19, No. 20, No. 21, No. 22, No. 23, No. 24, No. 25, No. 26, No. 27 and No. 28 and combinations thereof.

In the present invention, the term "peptide" is also intended to denote the oligomeric polypeptides comprising at least 4 repeat sequences selected from SEQ ID No. 5, No. 6, No. 7, No. 8, No. 17, No. 18, No. 19, No. 20, No. 21, No. 22, No. 23, No. 24, No. 25, No. 26, No. 27 and No. 28 and combinations thereof.

In the present invention, the term "peptide" is also intended to denote the oligomeric polypeptides comprising at least 5 repeat sequences selected from SEQ ID No. 5, No. 6, No. 7, No. 8, No. 17, No. 18, No. 19, No. 20, No. 21, No. 22, No. 23, No. 24, No. 25, No. 26, No. 27 and No. 28 and combinations thereof.

In the present invention, the term "peptide" is also intended to denote the oligomeric polypeptides comprising at least 6 repeat sequences selected from SEQ ID No. 5, No. 6, No. 7, No. 8, No. 17, No. 18, No. 19, No. 20, No. 21, No. 22, No. 23, No. 24, No. 25, No. 26, No. 27 and No. 28 and combinations thereof.

Advantageously, said peptide has at least 90% identity after optimum alignment with a sequence selected from SEQ ID No. 5, SEQ ID No. 6, SEQ ID No. 7, SEQ ID No. 8, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 or SEQ ID No. 28. Even more advantageously, said peptide has at least 100% identity after optimum alignment with a sequence selected from SEQ ID No. 5, SEQ ID No. 6, SEQ ID No. 7, SEQ ID No. 8, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 or SEQ ID No. 28 and combinations thereof.

"Percentage of identity" between two nucleic acid or amino acid sequences, in the sense of the present invention, denotes a percentage of nucleotides or amino acid residues that are identical between the two sequences to be compared, obtained after the best alignment (optimum alignment), this percentage being purely statistical and the differences between the two sequences being distributed randomly and along their entire length. Sequence comparisons between two nucleic acid or amino acid sequences are performed conventionally by comparing these sequences after their optimum alignment, and said comparison can be effected per segment or per "comparison window". As well as being performed manually, optimum alignment of the sequences for comparison can be performed by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444], by means of software using these algorithms (GAP, BESTFIT, FASTA and TFASTA in the Wisconsin Genetics Software Package, Genetics Computer Group, 575 Science Dr., Madison, Wis., or with the comparison software BLAST N, or BLAST P, ClustalW).

The percentage identity between two nucleic acid or amino acid sequences is determined by comparing these two optimally aligned sequences wherein the nucleic acid or amino acid sequence to be compared can comprise additions or deletions relative to the reference sequence for an optimum alignment between these two sequences. The percentage identity is calculated by determining the number of identical positions for which the nucleotide or the amino acid residue is identical between the two sequences, dividing this number of identical positions by the total number of positions in the comparison window and multiplying the result obtained by 100 to obtain the percentage identity between these two sequences.

For example, it would be possible to use the BLAST program, "BLAST 2 sequences" (Tatusova et al., "Blast 2 sequences—a new tool for comparing protein and nucleotide sequences", FEMS Microbiol Lett. 174:247-250) available on the website http://www.ncbi.nlm.nih.gov/gorf/b12.html, the parameters used being those given by default (in particular for the parameters "open gap penalty": 5, and "extension gap penalty": 2; the matrix selected being for example the "BLOSUM 62" matrix suggested by the program), the percentage identity between the two sequences to be compared being calculated directly by the program.

As the amino acid sequence having at least 80%, and preferably 85%, 90%, 95% and 98% identity with a reference amino acid sequence, those are preferred that have certain modifications relative to the reference sequence, in particular a deletion, addition or substitution of at least one amino acid, a truncation or an extension. In the case of a substitution, of one or more consecutive or non-consecutive amino acid(s), substitutions are preferred in which the substituted amino acids are replaced with "equivalent" amino acids. Here, the expression "equivalent amino acids" denotes any amino acid that can be substituted for one of the amino acids of the base structure though without essentially modifying the biological activities of the corresponding antibodies and as will be defined later, notably in the examples.

These equivalent amino acids can be determined either on the basis of their structural homology with the amino acids for which they are substituted, or on the basis of the results of comparative tests of biological activity between the various peptides and/or between the various fragments of intermediate filaments.

We may mention, as an example, the possibilities of substitution that can be effected without leading to a marked change in the biological activity of the corresponding modified peptide. Thus, leucine can be replaced with valine or isoleucine, aspartic acid with the acid glutamine, glutamine with asparagine, arginine with lysine, etc., and the inverse substitutions can of course be envisaged in the same conditions. Finally, modifications of the amino acids (for example phosphorylation, biotinylation, acetylation, etc.), which may make the biological activity of these peptides more effective, can also be envisaged.

The invention also relates to a peptide of sequence selected from SEQ ID No. 5, SEQ ID No. 6, SEQ ID No. 7, SEQ ID No. 8, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27 or SEQ ID No. 28.

The present invention also relates to a peptide of sequence SEQ ID No. 5, called Neurofilament Light subunit-Tubulin Binding Site 1 (NFL-TBS1).

NFL-TBS1 denotes the polypeptide responsible for binding to the tubulin derived from the neurofilament subunit of low molecular weight capable of binding tubulin.

"Low molecular weight" means between 1 and 70 kDa, preferably 34 kDa.

The present invention also relates to a peptide of sequence SEQ ID No. 6, called Neurofilament Light subunit-Tubulin Binding Site 2 (NFL-TBS2).

NFL-TBS2 denotes the polypeptide responsible for binding to the tubulin derived from the neurofilament subunit of low molecular weight capable of binding tubulin.

"Low molecular weight" means between 1 and 70 kDa, preferably 34 kDa.

The present invention also relates to a peptide of sequence SEQ ID No. 7, called Neurofilament Medium subunit-Tubulin Binding Site (NFM-TBS).

NFM-TBS denotes the polypeptide responsible for binding to the tubulin derived from the neurofilament subunit of medium molecular weight capable of binding tubulin.

"Medium molecular weight" means between 1 and 170 kDa, preferably 150 kDa.

The present invention also relates to a peptide of sequence SEQ ID No. 8, called Neurofilament high subunit-Tubulin Binding Site (NFH-TBS).

NFH-TBS denotes the polypeptide responsible for binding to the tubulin derived from the neurofilament subunit of high molecular weight capable of binding tubulin.

"Considerable molecular weight" means a molecular weight greater than 170 kDa, preferably 200 kDa.

The present invention also relates to a peptide of sequence SEQ ID No. 17, called Desmin-Tubulin Binding Site (Des-TBS1). Des-TBS1 denotes the polypeptide responsible for binding to the tubulin derived from desmin, capable of binding tubulin.

The present invention also relates to a peptide of sequence SEQ ID No. 18, called Desmin-Tubulin Binding Site (Des-TBS2). Des-TBS2 denotes the polypeptide responsible for binding to the tubulin derived from desmin, capable of binding tubulin.

The present invention also relates to a peptide of sequence SEQ ID No. 19, called Desmin-Tubulin Binding Site (Des-TBS3). Des-TBS3 denotes the polypeptide responsible for binding to the tubulin derived from desmin, capable of binding tubulin.

The present invention also relates to a peptide of sequence SEQ ID No. 20, called Vimentin-Tubulin Binding Site (Vim-TBS1). Vim-TBS1 denotes the polypeptide responsible for binding to the tubulin derived from vimentin, capable of binding tubulin.

The present invention also relates to a peptide of sequence SEQ ID No. 21, called Vimentin-Tubulin Binding Site (Vim-TBS2). Vim-TBS2 denotes the polypeptide responsible for binding to the tubulin derived from vimentin, capable of binding tubulin.

The present invention also relates to a peptide of sequence SEQ ID No. 22, called Vimentin-Tubulin Binding Site (Vim-TBS3). Vim-TBS3 denotes the polypeptide responsible for binding to the tubulin derived from vimentin, capable of binding tubulin.

The present invention also relates to a peptide of sequence SEQ ID No. 23, called Cytokeratin-Tubulin Binding Site (Ker-TBS1). Ker-TBS1 denotes the polypeptide responsible for binding to the tubulin derived from cytokeratin, capable of binding tubulin.

The present invention also relates to a peptide of sequence SEQ ID No. 24, called Cytokeratin-Tubulin Binding Site (Ker-TBS2). Ker-TBS2 denotes the polypeptide responsible for binding to the tubulin derived from cytokeratin, capable of binding tubulin.

The present invention also relates to a peptide of sequence SEQ ID No. 25, called Cytokeratin-Tubulin Binding Site (Ker-TBS3). Ker-TBS3 denotes the polypeptide responsible for binding to the tubulin derived from cytokeratin, capable of binding tubulin.

The present invention also relates to a peptide of sequence SEQ ID No. 26, called Glial Fibrillary Acidic Protein-Tubulin Binding Site (GFAP-TBS1). GFAP-TBS1 denotes the polypeptide responsible for binding to the tubulin derived from GFAP, capable of binding tubulin.

The present invention also relates to a peptide of sequence SEQ ID No. 27, called Glial Fibrillary Acidic Protein-Tubulin Binding Site (GFAP-TBS2). GFAP-TBS2 denotes the polypeptide responsible for binding to the tubulin derived from GFAP, capable of binding tubulin.

The present invention also relates to a peptide of sequence SEQ ID No. 28, called Glial Fibrillary Acidic Protein-Tubulin Binding Site (GFAP-TBS3). GFAP-TBS3 denotes the polypeptide responsible for binding to the tubulin derived from GFAP, capable of binding tubulin.

According to the present invention, said peptides can notably be obtained by conventional peptide chemical synthesis or by the recombinant route, which are familiar to a person skilled in the art.

The methods of preparation of recombinant peptides are now well known by a person skilled in the art and will not be discussed in detail in the present description. Among the cells that can be used for the production of these recombinant proteins, we may notably mention bacterial cells, and more particularly *E. coli*.

The alteration of tubulin polymerization is measured by measuring the turbidity (optical density at 350 nm) of a tubulin suspension. A decrease in turbidity of at least 1% is a sign of inhibition of tubulin polymerization.

The present invention also relates to an isolated nucleic acid coding for one of the peptides according to the present invention.

Nucleic acid denotes, according to the present invention, DNA or RNA.

The invention therefore relates to an isolated nucleic acid coding for a fragment of intermediate filament capable of altering tubulin polymerization.

In particular, the invention relates to an isolated nucleic acid coding for a fragment of particular intermediate filaments, the neurofilaments, said fragment being capable of altering tubulin polymerization.

In particular, the invention relates to an isolated nucleic acid coding for a particular fragment of intermediate filament, the protein desmin, said fragment being capable of altering tubulin polymerization.

In particular, the invention relates to an isolated nucleic acid coding for a particular fragment of intermediate filament, the protein vimentin, said fragment being capable of altering tubulin polymerization.

In particular, the invention relates to an isolated nucleic acid coding for a particular fragment of intermediate filament, the protein cytokeratin, said fragment being capable of altering tubulin polymerization.

In particular, the invention relates to an isolated nucleic acid coding for a particular fragment of intermediate filament, the protein Glial Fibrillary Acidic Protein (GFAP), said fragment being capable of altering tubulin polymerization.

Thus, the invention relates to a nucleic acid having at least 80% and preferably 85%, 90%, 95%, 98% and 100% of identity after optimum alignment with a sequence selected from SEQ ID No. 1, SEQ ID No. 2, SEQ ID No. 3, SEQ ID No. 4, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39 or SEQ ID No. 40.

More particularly, the present invention relates to a nucleic acid having at least 80% and preferably 85%, 90%, 95%, 98% and 100% of identity after optimum alignment with sequence SEQ ID No. 1, coding for a peptide of amino acid sequence SEQ ID No. 5, called NFL-TBS1.

More particularly, the present invention relates to a nucleic acid having at least 80% and preferably 85%, 90%, 95%, 98% and 100% of identity after optimum alignment with sequence SEQ ID No. 2, coding for a peptide of amino acid sequence SEQ ID No. 6, called NFL-TBS2.

More particularly, the present invention relates to a nucleic acid having at least 80% and preferably 85%, 90%, 95%, 98% and 100% of identity after optimum alignment with sequence SEQ ID No. 3, coding for a peptide of amino acid sequence SEQ ID No. 7, called NFM-TBS.

More particularly, the present invention relates to a nucleic acid having at least 80% and preferably 85%, 90%, 95%, 98% and 100% of identity after optimum alignment with sequence SEQ ID No. 4, coding for a peptide of amino acid sequence SEQ ID No. 8, called NFH-TBS.

More particularly, the present invention relates to a nucleic acid having at least 80% and preferably 85%, 90%, 95%, 98% and 100% of identity after optimum alignment with sequence SEQ ID No. 29, coding for a peptide of amino acid sequence SEQ ID No. 17, called Des-TBS1.

More particularly, the present invention relates to a nucleic acid having at least 80% and preferably 85%, 90%, 95%, 98% and 100% of identity after optimum alignment with sequence SEQ ID No. 30, coding for a peptide of amino acid sequence SEQ ID No. 18, called Des-TBS2.

More particularly, the present invention relates to a nucleic acid having at least 80% and preferably 85%, 90%, 95%, 98% and 100% of identity after optimum alignment with sequence SEQ ID No. 31, coding for a peptide of amino acid sequence SEQ ID No. 19, called Des-TBS3.

More particularly, the present invention relates to a nucleic acid having at least 80% and preferably 85%, 90%, 95%, 98% and 100% of identity after optimum alignment with sequence SEQ ID No. 32, coding for a peptide of amino acid sequence SEQ ID No. 20, called Vim-TBS1.

More particularly, the present invention relates to a nucleic acid having at least 80% and preferably 85%, 90%, 95%, 98% and 100% of identity after optimum alignment with sequence SEQ ID No. 33, coding for a peptide of amino acid sequence SEQ ID No. 21, called Vim-TBS2.

More particularly, the present invention relates to a nucleic acid having at least 80% and preferably 85%, 90%, 95%, 98% and 100% of identity after optimum alignment with sequence SEQ ID No. 34, coding for a peptide of amino acid sequence SEQ ID No. 22, called Vim-TBS3.

More particularly, the present invention relates to a nucleic acid having at least 80% and preferably 85%, 90%, 95%, 98% and 100% of identity after optimum alignment with sequence SEQ ID No. 35, coding for a peptide of amino acid sequence SEQ ID No. 23, called Ker-TBS1.

More particularly, the present invention relates to a nucleic acid having at least 80% and preferably 85%, 90%, 95%, 98% and 100% of identity after optimum alignment with sequence SEQ ID No. 36, coding for a peptide of amino acid sequence SEQ ID No. 24, called Ker-TBS2.

More particularly, the present invention relates to a nucleic acid having at least 80% and preferably 85%, 90%, 95%, 98% and 100% of identity after optimum alignment with sequence SEQ ID No. 37, coding for a peptide of amino acid sequence SEQ ID No. 25, called Ker-TBS3.

More particularly, the present invention relates to a nucleic acid having at least 80% and preferably 85%, 90%, 95%, 98% and 100% of identity after optimum alignment with sequence SEQ ID No. 38, coding for a peptide of amino acid sequence SEQ ID No. 26, called GFAP-TBS1.

More particularly, the present invention relates to a nucleic acid having at least 80% and preferably 85%, 90%, 95%, 98% and 100% of identity after optimum alignment with sequence SEQ ID No. 39, coding for a peptide of amino acid sequence SEQ ID No. 27, called GFAP-TBS2.

More particularly, the present invention relates to a nucleic acid having at least 80% and preferably 85%, 90%, 95%, 98% and 100% of identity after optimum alignment with sequence SEQ ID No. 40, coding for a peptide of amino acid sequence SEQ ID No. 28, called GFAP-TBS3.

The present invention also relates to a vector that comprises a nucleic acid according to the present invention. Said nucleic acid is advantageously selected from the group comprising SEQ ID No. 1, SEQ ID No. 2, SEQ ID No. 3, SEQ ID No. 4, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39 and SEQ ID No. 40.

Vector means, according to the present invention, a plasmid, a cosmid, a phage, a BAC (Bacterial Artificial Chromosome), a YAC (Yeast Artificial Chromosome) or any other DNA fragment capable of replicating in a cell.

The present invention also relates to a host cell which is transformed by a nucleic acid according to the present invention or a vector according to the present invention. Said nucleic acid is advantageously selected from the group comprising SEQ ID No. 1, SEQ ID No. 2, SEQ ID No. 3, SEQ ID No. 4, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39 and SEQ ID No. 40.

Host cell means, according to the present invention, both eukaryotic and prokaryotic cells. Among the eukaryotic cells that are suitable, we may mention animal, vegetable and bacterial cells, yeasts, fungi or embryonic stem cells (mouse, rat, human, and of all species in general). In particular, regarding yeasts, we may mention yeasts of the genus *Saccharomyces, Kluyveromyces, Pichia, Schwanniomyces* or *Hansenula*. Regarding animal cells, we may mention COS, CHO, C127 cells, *Xenopus* eggs, etc. Among the fungi, we may mention more particularly *Micromonospora, Aspergillus* ssp. or *Trichoderma* ssp. As prokaryotic cells, it is preferable to use the following bacteria: *Actinomycetes*, and notably *Streptomyces, E. coli*, or *Bacillus*.

The host cells according to the present invention can be transformed by any method permitting a foreign nucleic sequence to be inserted in a cell. This may notably be transformation, electroporation, conjugation, fusion of protoplasts, or any other technique known by a person skilled in the art.

The present invention also relates to a method of production of recombinant peptide according to the present invention, characterized in that it comprises the following stages:
a) culture of a cell according to the present invention in a suitable culture medium and in suitable culture conditions,
b) recovery of said peptide from the cells or from the culture medium obtained in stage a).

The present invention also relates to a pharmaceutical composition comprising a peptide according to the present invention and/or obtained by a method according to the present invention, with a pharmaceutically acceptable vehicle.

"Pharmaceutically acceptable vehicle" means, according to the present invention, carriers and vehicles that can be administered to a human being or to an animal.

The present invention also relates to the use of a peptide according to the present invention and/or obtained by a method according to the present invention for inhibiting cell proliferation and/or cell mobility.

"Cell proliferation" means, according to the present invention, a succession of rapid divisions of cells or of microorganisms. Microorganisms also means endoparasites.

"Cells" means notably all cells that have a microtubule cytoskeleton, for example the cells of a given tissue such as the lung, liver, breast, or the blood vessels, but also free cells such as spermatozoa, ova, or blood platelets.

Cell division leads to homogeneous cell populations, which may or may not be organized as tissues. It is sometimes accompanied by a certain degree of structural anarchy, even culminating in loss of shape and of characteristic properties. Cell proliferations are observed notably during processes of an inflammatory or tumoral nature.

This phenomenon, which is normal during development and growth for the majority of tissues and permanently for certain cell lines (formed elements of the blood, spermatic line, etc.), becomes abnormal in certain conditions; it leads to the formation of neoformed or neoplastic tissues.

A process that is essential to tumor growth and involves cell proliferation is angiogenesis. A peptide according to the invention can therefore be used notably for inhibiting angiogenesis during tumor growth.

The peptide according to the present invention can also be used for inhibiting bacterial multiplication or the proliferation of certain plants such as algae or lichens or fungi, which have a microtubule cytoskeleton. More particularly, the peptide according to the present invention can be used for inhibiting the development of parasites and more particularly endoparasites in foods.

Tubulin, once it is polymerized as microtubules, plays an essential role in axonal transport, acting as rails along which the organelles move in both directions—anterograde and retrograde—owing to specific driving proteins. The peptide according to the present invention is able to cross the cell membrane. Moreover, said peptide, by blocking the polymerization of tubulin to microtubule, and being capable of binding to tubulin, it makes it possible to block intracellular transport and the fixation of driving proteins.

Thus, the present invention also relates to the use of a peptide according to the present invention for blocking intracellular transport and/or cell mobility.

Furthermore, said peptide blocks the polymerization of tubulin to microtubule by binding to tubulin. Accordingly, owing to this binding, it is possible to label tubulin and the microtubules with said peptide.

Thus, the present invention also relates to the use of a peptide according to the present invention as marker of tubulin and of the microtubules.

The present invention also relates to the use of a peptide according to the present invention and/or obtained by a method according to the present invention, for the production of medicinal products.

According to the present invention, the medicinal product is intended for preventing or treating diseases involving cell proliferation and/or cell motility.

The following may be mentioned as examples of diseases involving cell proliferation and/or cell motility according to the present invention: cancers, bacterial infections or diseases involving proliferation of certain plants such as algae or lichens, or psoriasis.

More particularly, according to the present invention, the medicinal product is intended for preventing or treating cancers.

"Cancer" means, according to the present invention, one or more tumors composed of atypical cells, characterized by a capacity for independent growth, imprecise delimitation, ability to invade neighboring tissues and vessels, and a tendency to spread by production of metastases.

There are two main categories of malignant tumors: carcinomas, of epithelial origin, and sarcomas, of conjunctive origin. There are also embryonic tumors. The term cancer is a general term denoting all malignant neoplastic formations, whatever their histologic nature.

Even more particularly, according to the present invention, the medicinal product is intended for preventing or treating cancer of the nervous system, liver cancer, prostate cancer or skin cancer.

Preferably, according to the present invention, the cancer is a cancer of the nervous system.

Moreover, the peptide according to the present invention has an effect at the sites of interaction between tubulin and the intermediate filaments, these sites being liable to undergo mutation in genetic diseases. In fact, in the case when the interaction between tubulin and an intermediate filament is necessary for activation of an enzyme (for example a kinase or phosphatase during normal division), a mutation at the site of interaction prevents activation of said enzyme. Addition of a normal peptide then makes it possible to restore interaction between tubulin and the peptide and therefore activation of the enzyme. The present invention therefore also relates to the use of a peptide according to the present invention for production of a medicinal product intended for the treatment of genetic diseases.

The present invention also relates to the use of a peptide according to the present invention and/or obtained by a method according to the present invention for detecting and/or testing products that are liable to block the interaction between tubulin and said peptide.

The present invention also relates to the use of a fragment of intermediate filament capable of altering tubulin polymerization to inhibit cell proliferation and/or cell mobility.

The present invention also relates to the use of a fragment of intermediate filament capable of altering tubulin polymerization to block intracellular transport and the fixation of driving proteins.

The present invention also relates to the use of a fragment of intermediate filament capable of altering tubulin polymerization as a tubulin marker.

The present invention also relates to the use of a fragment of intermediate filament capable of altering tubulin polymerization for the production of medicinal products.

The present invention also relates to the use of a fragment of intermediate filament for detecting and/or testing products that are able to block the interaction between tubulin and said fragment of intermediate filament.

More particularly, a fragment of intermediate filament can be the cytokeratin endoA of sequence SEQ ID No. 9, keratin 8 of sequence SEQ ID No. 10, peripherin of sequence SEQ ID No. 11, α-internexin of sequence SEQ ID No. 12, GFAP of sequence SEQ ID No. 13 or vimentin of sequence SEQ ID No. 14.

Sequences SEQ ID No. 9 and SEQ ID No. 10 are identical.

According to bioinformatic analyses, notably using the program Clustal W (cf. Table 1), sequence homology exists between the cytokeratin endoA which has at least 80%, and preferably 85%, 90%, 98% and 100% of identity after optimum alignment with sequence SEQ ID No. 9, keratin 8 which has at least 80%, and preferably 85%, 90%, 98% and 100% of identity after optimum alignment with sequence SEQ ID No. 10, peripherin which has at least 80%, and preferably 85%, 90%, 98% and 100% of identity after optimum alignment with sequence SEQ ID No. 11, α-internexin which has at least 80%, and preferably 85%, 90%, 98% and 100% of identity after optimum alignment with sequence SEQ ID No. 12, GFAP which has at least 80%, and preferably 85%, 90%, 98% and 100% of identity after optimum alignment with sequence SEQ ID No. 13, or vimentin which has at least 80%, and preferably 85%, 90%, 98% and 100% of identity after optimum alignment with sequence SEQ ID No. 14.

According to bioinformatic analysis, it appears that a peptide according to the present invention and/or a fragment of intermediate filament according to the present invention has an active structural unit which can be imitated by a synthetic molecule, and this synthetic molecule can be used instead of the peptide.

The present invention therefore also relates to a synthetic molecule having an active structural unit similar to a peptide according to the present invention and/or obtained by a method according to the present invention, and/or a fragment of intermediate filament according to the present invention.

The synthetic molecule according to the present invention can have the same uses as the peptide according to the present invention and/or as the fragment of intermediate filament according to the present invention.

Knowing that the intermediate filaments, for example neurofilaments, interact with tubulin, the peptide derived from the tubulin sequence and corresponding to the site of interaction with the intermediate filaments can be used for fixing the intermediate filaments, or a fragment of intermediate filament, or of other molecules involved in cell division.

Thus, the present invention also relates to a tubulin peptide capable of binding to a peptide according to the present invention and/or obtained by a method according to the present invention and/or a fragment of intermediate filament according to the present invention.

The present invention also relates to a tubulin peptide that corresponds to the site of interaction with a peptide derived from intermediate filament of sequence SEQ ID No. 5 called NFL-TBS1.

The present invention also relates to a tubulin peptide that corresponds to the site of interaction with a peptide derived from intermediate filament of sequence SEQ ID No. 6 called NFL-TBS2.

The present invention also relates to a tubulin peptide that corresponds to the site of interaction with a peptide derived from intermediate filament of sequence SEQ ID No. 7 called NFM-TBS.

The present invention also relates to a tubulin peptide that corresponds to the site of interaction with a peptide derived from intermediate filament of sequence SEQ ID No. 8 called NFH-TBS.

The present invention also relates to a tubulin peptide that corresponds to the site of interaction with a peptide derived from intermediate filament of sequence SEQ ID No. 17 called Des-TBS1.

The present invention also relates to a tubulin peptide that corresponds to the site of interaction with a peptide derived from intermediate filament of sequence SEQ ID No. 18 called Des-TBS2.

The present invention also relates to a tubulin peptide that corresponds to the site of interaction with a peptide derived from intermediate filament of sequence SEQ ID No. 19 called Des-TBS3.

The present invention also relates to a tubulin peptide that corresponds to the site of interaction with a peptide derived from intermediate filament of sequence SEQ ID No. 20 called Vim-TBS1.

The present invention also relates to a tubulin peptide that corresponds to the site of interaction with a peptide derived from intermediate filament of sequence SEQ ID No. 21 called Vim-TBS2.

The present invention also relates to a tubulin peptide that corresponds to the site of interaction with a peptide derived from intermediate filament of sequence SEQ ID No. 22 called Vim-TBS3.

The present invention also relates to a tubulin peptide that corresponds to the site of interaction with a peptide derived from intermediate filament of sequence SEQ ID No. 23 called Ker-TBS1.

The present invention also relates to a tubulin peptide that corresponds to the site of interaction with a peptide derived from intermediate filament of sequence SEQ ID No. 24 called Ker-TBS2.

The present invention also relates to a tubulin peptide that corresponds to the site of interaction with a peptide derived from intermediate filament of sequence SEQ ID No. 25 called Ker-TBS3.

The present invention also relates to a tubulin peptide that corresponds to the site of interaction with a peptide derived from intermediate filament of sequence SEQ ID No. 26 called GFAP-TBS1.

The present invention also relates to a tubulin peptide that corresponds to the site of interaction with a peptide derived from intermediate filament of sequence SEQ ID No. 27 called GFAP-TBS2.

The present invention also relates to a tubulin peptide that corresponds to the site of interaction with a peptide derived from intermediate filament of sequence SEQ ID No. 28 called GFAP-TBS3.

The present invention also relates to a tubulin peptide that corresponds to the site of interaction with a fragment of intermediate filament of sequence SEQ ID No. 9 called cytokeratin endoA.

The present invention also relates to a tubulin peptide that corresponds to the site of interaction with a fragment of intermediate filament of sequence SEQ ID No. 10 called keratin 8.

The present invention also relates to a tubulin peptide that corresponds to the site of interaction with a fragment of intermediate filament of sequence SEQ ID No. 11 called peripherin.

The present invention also relates to a tubulin peptide that corresponds to the site of interaction with a fragment of intermediate filament of sequence SEQ ID No. 12 called α-internexin.

The present invention also relates to a tubulin peptide that corresponds to the site of interaction with a fragment of intermediate filament of sequence SEQ ID No. 13 called GFAP.

The present invention also relates to a tubulin peptide that corresponds to the site of interaction with a fragment of intermediate filament of sequence SEQ ID No. 14 called vimentin.

As a result of this fixation, the tubulin peptides according to the present invention serve as a decoy, since the molecules that are essential for cell division will attach to this peptide, and so, will no longer be available for attaching to tubulin, and will therefore no longer be available for cell division.

Thus, the present invention also relates to a use of said tubulin peptide for blocking cell division and/or cell mobility. The present invention also relates to a use of said tubulin peptide for blocking the binding of tubulin to the intermediate filaments and thus make it possible for all the available tubulin to be used for forming microtubules. This use of said peptide as term and can be envisaged within the scope of axonal regeneration.

As tubulin is also the biological medium of intracellular transport, the present invention relates to the use of said tubulin peptide for blocking intracellular transport and fixation of driving proteins.

As tubulin is also the biological medium for the fixation of molecules on the microtubules, the present invention relates to the use of said tubulin peptide for blocking the fixation of molecules on the microtubules.

Knowing, moreover, that the neurofilaments (like other intermediate filaments) disappear during cell division, it is very probable that this type of fixation is crucial to their disappearance, for example by activation of proteolysis.

The uses according to the present invention of the peptide derived from the intermediate filaments, of the fragment of intermediate filament, and of the peptide derived from tubulin are possible both in animals and plants or microorganisms, therefore in the pharmaceutical, clinical, agrochemical and agriculture and food sectors.

The present invention will be better understood from the rest of the description given below, which refers to an example showing that tubulin and the neurofilaments are binding partners and we shall demonstrate that this interaction plays a critical role in modulation of the dynamics of the neuronal microtubules.

Of course, this example is only given for purposes of illustrating the object of the invention and it should not be regarded in any way as a limitation thereof.

FIGURE CAPTIONS

FIG. 1. Tubulin co-purified with neurofilaments at 4° C. preserves its properties of polymerizability to microtubule and is a protein associated with the three subunits of the neurofilaments.

(A): Using antibodies directed against the various isotypes of tubulin ($\alpha$, $\beta$, $\beta$III, $\gamma$ and polyglutamylated), tubulin was detected in each of the fractions of a conventional preparation of neurofilaments. Despite incubation at 4° C. or the presence of colchicine, a large amount of tubulin is systematically co-purified with the neurofilaments.

(B): When a deposit P3 incubated at 4° C. without colchicine is observed in an electron microscope, no microtubule can be detected on the microscopy grid (data not shown). However, when this preparation is incubated at 37° C. in the presence of GTP, numerous microtubules are observed with the neurofilaments. Some neurofilaments are decorated with amorphous material which could be tubulin (bar: 100 nm).

(C): 40 μg of NF was incubated for 1 hour in the presence of tubulin that had been purified then centrifuged at 100000 g for 30 min. Western blotting of the supernatants and deposits shows that the tubulin present in the deposits increases in proportion to the amount of exogenous tubulin added for incubation up to a plateau, which shows that the NF-tubulin interaction is saturable.

(D): The proteins present in deposit P3 were separated by SDS-PAGE and transferred to a PVDF membrane, then incubated with tubulin purified on a phosphocellulose column. The membranes were then incubated with an anti-$\beta$III tubulin antibody before proceeding with conventional Western blotting. The results show that tubulin interacts with the bands corresponding to NFL, NFM, and the phosphorylated form of NFH, $\alpha$- and $\beta$-tubulin, as well as with synapsin* and MAPS** (1). When a similar experiment is performed in the absence of tubulin, only a band corresponding to $\beta$III-tubulin is observed (2). The same membrane (1) was hybridized successively with the various antibodies anti-NFL (3), anti-NFM (4), and anti-NFH (5). The anti-NFH antibody recognizes the two phosphorylated and unphosphorylated forms of NFH.

FIG. 2. Tubulin binds to the N-terminal end of each of the subunits of the neurofilaments. Effect of each of the sequences corresponding to this binding site on polymerization of the microtubules.

(A): Peptide array membranes were incubated as in the procedure described by Frank and Owerwin (1996) with tubulin purified on a phosphocellulose column overnight at 4.degree. C. The tubulin fixed was detected with an anti-.beta.III tubulin antibody and a secondary antibody coupled to peroxidase. The NFL subunit contains two tubulin binding domains (called NFL-TBS1 (SEQ ID NO: 5) and NFL-TBS2 (SEQ ID NO: 6)), whereas NFM and NFH contain a single binding sequence of 39 amino acids (called NFM-TBS (SEQ ID NO: 7) and NFH-TBS (SEQ ID NO: 8) respectively).

(B): Each of these peptides corresponding to the tubulin binding site were tested in vitro for their effect on tubulin polymerization to microtubules at various concentrations: 100 μM (•), 30 μM (♦), 10 μM (▼), 3 μM (▲) or without peptide (■). (1): NFL-TBS1, (2): NFL-TBS2, (3): NFM-TBS and (4): NFH-TBS. (5): curve of the inhibitory effect of each peptide as a function of log concentration.

Figure 3A:
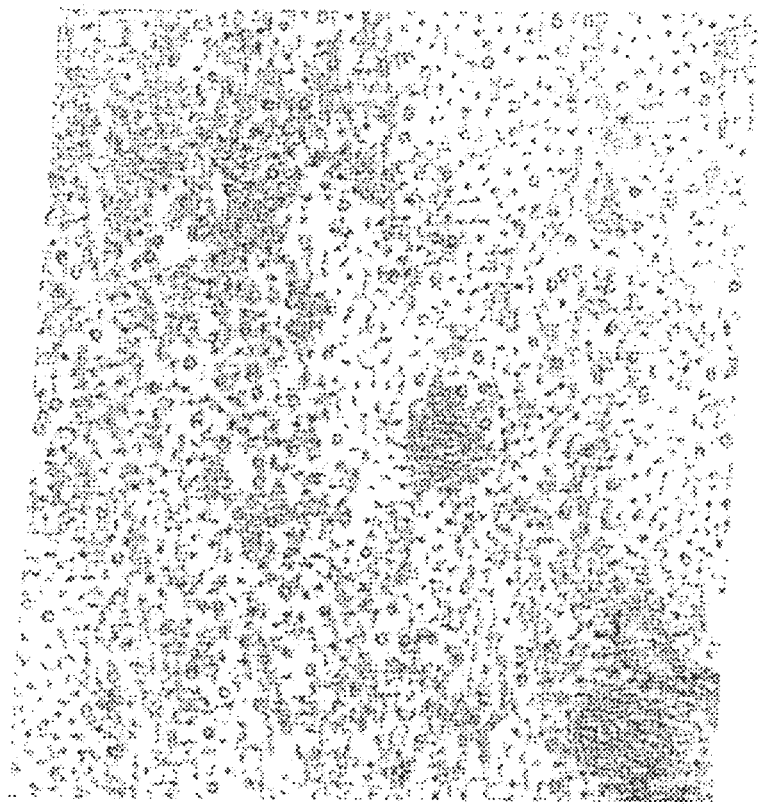
Figure 3B:
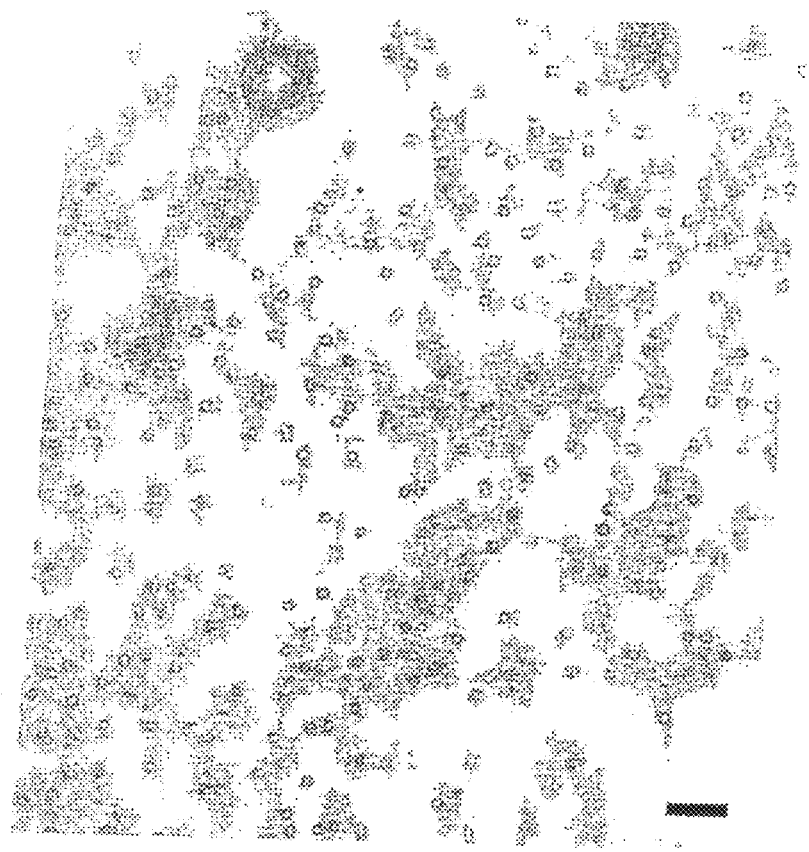

FIG. 3. Electron micrographs of cross sections of axons of control and transgenic mice.

The neurofilaments observed in the axons of control mice are absent from the axons of transgenic mice (bar=100 nm).

FIG. 4. The amount of mRNA of $\alpha$-tubulin present in the control and NFHLacZ mice is the same.

(A): During development the amount of mRNA of tubulin Mal falls by a factor of 10 both in the brain and in the spinal cord. A similar expression profile is observed between the two genotypes.

(B): The levels of mRNA of tubulin M$\alpha$2 remain constant during development, both in the brain and in the spinal cord, without any difference between controls and transgenics. (−: controls, +: transgenics, 2D: 2 days, 4 w: 4 weeks, ad: adults, and n represents the number of brains and spinal cords used for carrying out the experiments in triplicate).

(C): mRNAs of tubulin M$\alpha$3/7 were only detected in the testes. No ectopic expression was detected.

FIG. 5. The amount of mRNA of tubulin $\beta$ is also unchanged between the control (−) and transgenic (+) mice.

(A): The amount of mRNA of tubulin Mβ2 decreases both in the brain (factor of 3) and in the spinal cord (factor of 10) without any difference between the control and transgenic mice.

(B): mRNAs of tubulin Mβ3 were detected at similar levels in the transgenic and control mice.

(C): The mRNAs of tubulin Mβ4 have a two-phase profile in the brain and the spinal cord. At first the mRNA level increases between stages 2 days and 4 weeks by a factor of 3 in the brain and 5 in the spinal cord. Then the level decreases by a factor of 2 in the brain and the spinal cord without any major difference between the control and transgenic mice.

(D-E): Two transcripts for tubulin Mβ5 were identified in the brain and the spinal cord. Their expression profile is similar between the control and transgenic mice. During development, the amount of the two transcripts decreases by a factor of 10. The larger transcript (2.8 kb) is expressed ten times more than the 1.8 kb transcript.

(F): A decrease by a factor of 5 in the brain and 3 in the spinal cord is observed for the mRNA level of tubulin Mβ6. This transcript is observed especially during the early stages of development without any difference between the two genotypes.

FIG. 6. The amount of tubulin present in the tissue homogenates from control and transgenic mice is not different.

(A): The amount of tubulin present in raw extracts from brains (B), spinal cord (SC) and sciatic nerves (SN) of control and transgenic mice is the same.

(B): The amount of tubulin present in the different fractions of a conventional preparation of microtubules is identical between the control and transgenic mice.

(C, D): To evaluate the capacity for polymerization of tubulin from control and transgenic mice, supernatants S1 of control and transgenic brains were incubated for 1 hour at 37° C. in the presence of GTP or in the presence of Taxol to induce polymerization of the MT (C), or in the cold or in the presence of colchicine to induce depolymerization of the microtubules (D). After centrifugation at 100000 g in the same conditions, the supernatants and deposits were analyzed by Western blotting using a panel of antibodies directed against the various tubulins. There is no difference between the control and transgenic mice.

Figure 7:
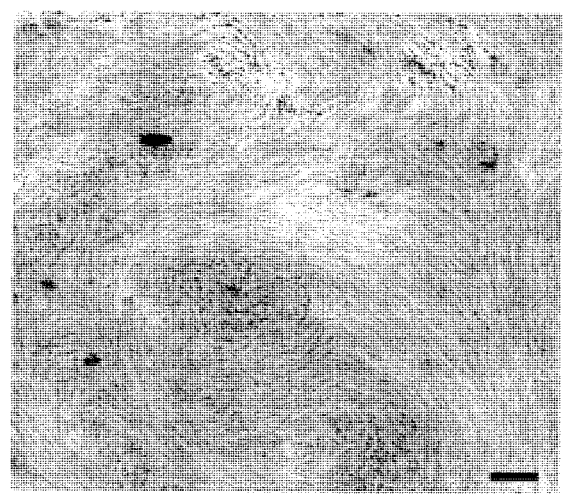
Figure 7:
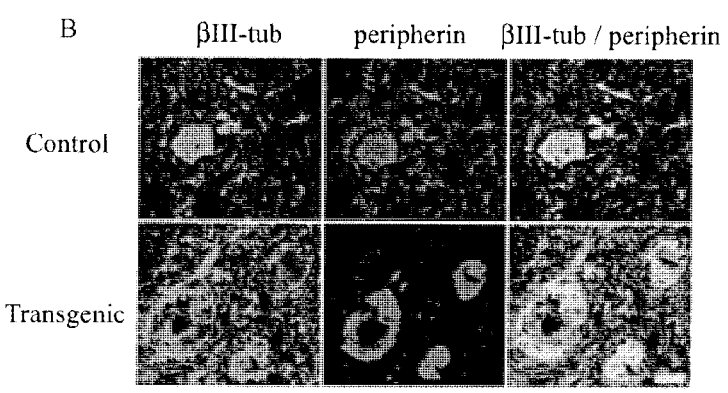

FIG. 7. In the electron microscope, no microtubule is observed in the aggregates of neurofilaments despite the presence of tubulin epitopes demonstrated by immunofluorescence coupled to confocal microscopy.

(A): Electron micrographs of an aggregate of neurofilaments present in the cell body of a mouse motoneuron. No microtubule can be seen (bar: 200 nm).

(B): Immunohistochemical analysis coupled to confocal microscopy of spinal cords of control and NFHLacZ mice using antibodies directed against tubulin βIII and peripherin. The two networks of neurofilaments and microtubules are co-localized in the cell body of the control mice. Despite the absence of microtubules in the cell body, the aggregates of neurofilaments contain tubulin epitopes (bar: 12.5 μm).

Figure 8:
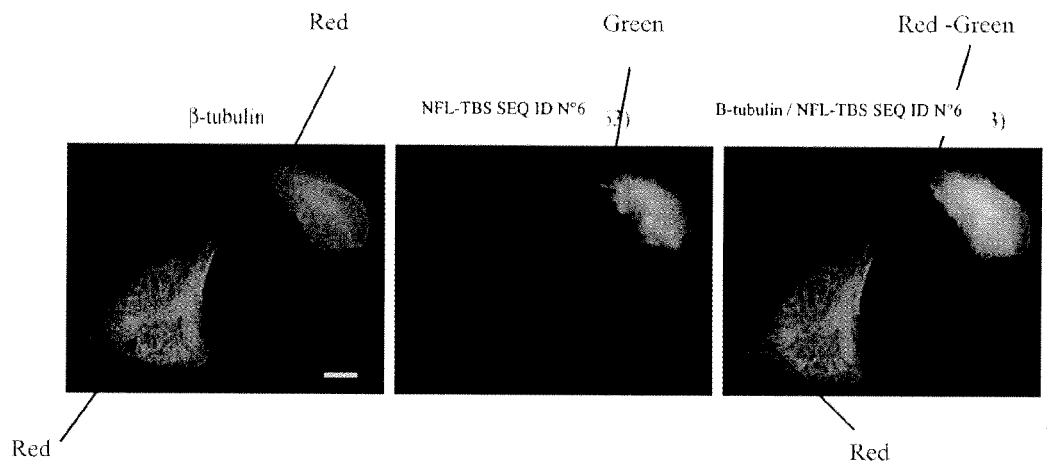
Figure 8:
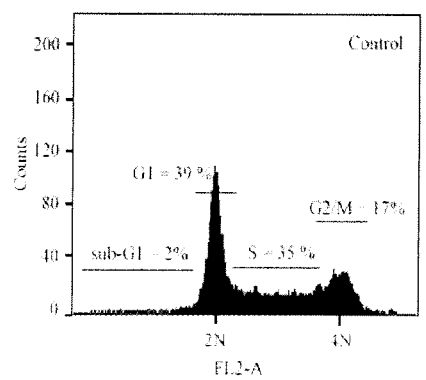
Figure 8:
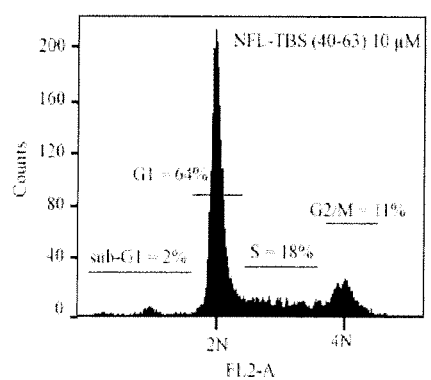
Figure 8:
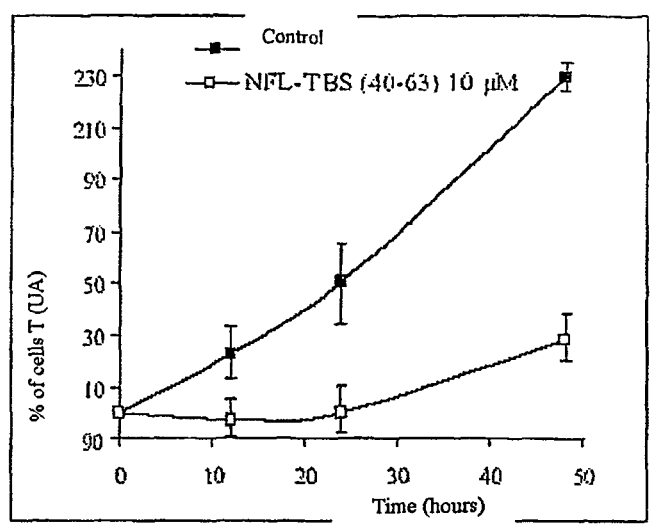

FIG. 8. Effect of the peptides NFL-TBS (SEQ ID No. 6) on the cytoskeleton of the microtubules and on cell division.

(A-A'-A"): The T98G cells are treated with the peptides SEQ ID No. 6 (10 μM) for 6 hours and the microtubules are then detected using an anti-tubulin antibody (red) and the biotinylated peptides SEQ ID No. 6 are detected using Alexa-labeled avidin (green). The cells that contain the peptides lack a typical microtubule network and are of a round shape whereas the normal cells have a normal network of microtubules.

(B-B'): Analysis by flow cytometry of control cells and cells treated with the peptides SEQ ID No. 6. The T98G cells treated with the peptides SEQ ID No. 6 (10 μM) for 48 hours show strong stopping in phase G1 compared with the control cells.

(C): Test of proliferation of T98G cells with the peptides SEQ ID No. 6: the proliferation of cells treated with the peptide (10 μM for 48 hours) is greatly reduced relative to the untreated control cells.

Figure 9A:
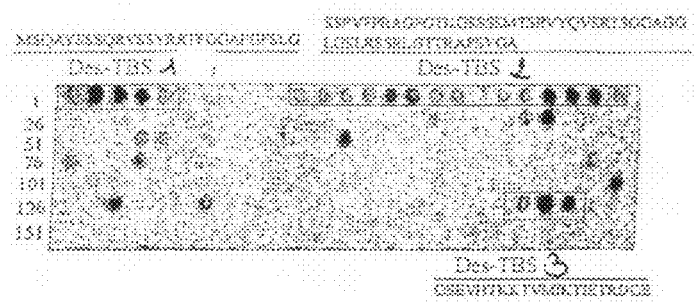
Figure 9B:
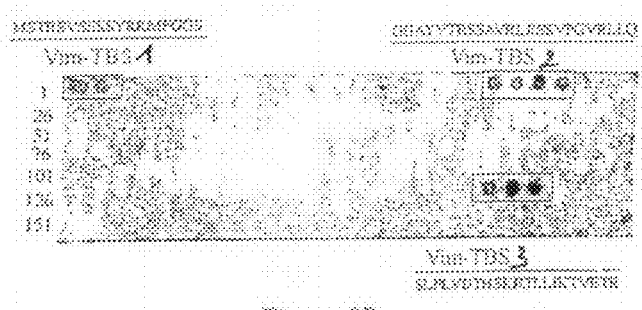
Figure 9C:
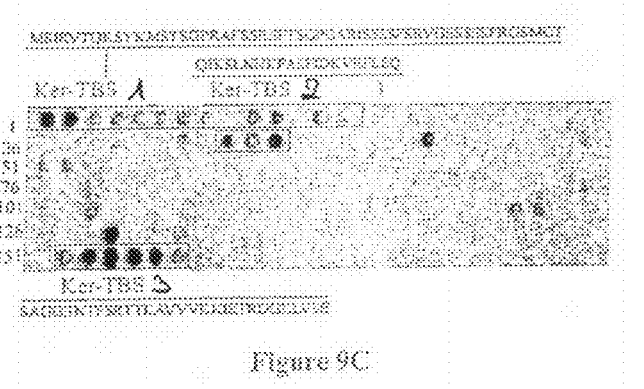
Figure 9D:
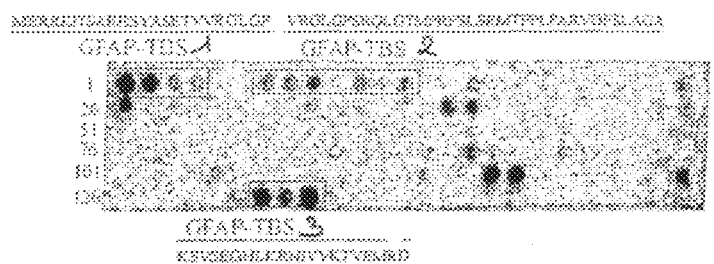

FIG. 9 (A, B, C, D):

Using the same experimental approach as that described for the neurofilament peptide chips, the peptide chips corresponding to the sequence of other intermediate filaments (A. Desmin, B. Vimentin, C. Cytokeratin and D. GFAP) were tested to detect the possible presence of a tubulin binding site. Each intermediate filament contains three tubulin binding sites (alignment of 2 points or more). Two sites are localized in the N-terminal domain and one in the C-terminal domain. FIG. 9A shows Des-TBS 1 (SEQ ID NO: 17), Des-TBS 2 (SEQ ID NO: 18), and Des-TBS 3 (SEQ ID NO: 19). FIG. 9B shows Vim-TBS 1 (SEQ ID NO: 20), Vim-TBS 2 (SEQ ID NO: 21), and Vim-TBS 3 (SEQ ID NO: 22). FIG. 9C shows Ker-TBS 1 (SEQ ID NO: 23), Ker-TBS 2 (SEQ ID NO: 24), and Ker-TBS 3 (SEQ ID NO: 25). FIG. 9D shows GFAP-TBS 1 (SEQ ID NO: 26), GFAP-TBS 2 (SEQ ID NO: 27), and GFAP-TBS 3 (SEQ ID NO: 28).

FIG. 10 (A, B, C, D, E):

Influence of the peptides Vim-TBS3 (SEQ ID No. 22), GFAP-TBS3 (SEQ ID No. 28), Ker-TBS1 (SEQ ID No. 23), Vim-TBS2 (SEQ ID No. 21) and GFAP-TBS1 (SEQ ID No. 26) on the polymerization of microtubules.

Using the same experimental approach as that described for the TBS peptides derived from neurofilaments, the influence on polymerization of microtubules was tested for A. Vim-TBS3 (SEQ ID No. 22), B. GFAP-TBS3 (SEQ ID No. 28), C. Ker-TBS1 (SEQ ID No. 23), D. Vim-TBS2 (SEQ ID No. 21) and E. GFAP-TBS1 (SEQ ID No. 26).

FIG. 11:

Effect of the peptide GFAP-TBS1 (SEQ ID No. 26) on cell division. Analysis by flow cytometry of control cells and cells treated with the peptide GFAP-TBS1 (SEQ ID No. 26). T98G cells treated with the peptide GFAP-TBS1 (SEQ ID No. 26) (100 μM) for 36 hours show strong stopping in phase G1 compared with the control cells.

EXAMPLES

Example 1

I Introduction

We shall now provide in vitro and in vivo proof that tubulin and the neurofilaments are binding partners and we shall demonstrate that this interaction plays a critical role in the modulation of the dynamics of neuronal microtubules. First, by applying series of conventional biochemical techniques, we showed that unpolymerized tubulin co-purifies with the assembled neurofilaments and interacts directly with the three subunits of neurofilaments. We then used an electron microscope to show that the unpolymerized tubulin associated with the neurofilaments maintains full capacity for assembling into microtubules. To investigate the extent and significance in vivo of this association, we used transgenic mice expressing the transgene NFHLacZ. These mice express low levels of NFH-β-galactosidase fusion proteins which crosslink the neurofilaments causing sequestration of the cytoskeleton of neurofilaments in the perikaryal aggregates.

We have demonstrated that neither the presence of perikaryal aggregates, nor the absence of neurofilaments in the axons of NFHLacZ transgenic mice (Eyer and Peterson, 1994) affects the accumulation of mRNA of the various isotypes of tubulins. Similarly, neither the total amount of tubulin protein recovered from the axons nor its potential for polymerization was altered in such neurons. However, axons that are deficient in neurofilaments have an attenuated radial growth reaching a diameter of only 50% relative to the normal and consequently their relative concentration of tubulin is atypically high. Consistently with their high tubulin concentration, the number and density of microtubules in such axons are greater than normal. However, the absolute number and the absolute density of microtubules far exceed what was predicted by the increase in tubulin concentration alone and therefore defines a major role for the neurofilaments in the regulation of the dynamics of the axonal microtubules. Conversely, inside the dense aggregates of neurofilaments that form in the neuronal perikaryon of NFHLacz mice, the tubulin epitopes are present but the profiles of microtubules could not be identified. Combined, these observations show that the neurofilaments and the unpolymerized tubulin are major binding partners and that this interaction affects the dynamics in vivo of the microtubules. Such integration of the cytoskeleton may play a role in sculpturing the axonal morphology with consequent effects in the function of fibres, both in physiological and pathological conditions.

II Material and Method

1. Data Analysis

The sequence alignments were carried out with ClustalW and were corrected manually. The very conserved central domain of each intermediate filament was used for anchoring the alignment. Table 1 was produced with the Genedoc software.

2. Analysis of the mRNAs by Northern Blotting

The brains and spinal cords were taken from NFHlacZ transgenic mice and control mice, at 2 days, 4 weeks, 6 months and 18 months and then frozen immediately in liquid nitrogen and stored at −80° C. The total RNAs were extracted by the method of Chomczynski and Sacchi (1987). 10 µg of RNA from each sample was used for carrying out electrophoresis on 1.2% agarose gel, containing 2.2 M of formaldehyde, and transferred by aspiration to a Nytran N nylon membrane (Schleicher and Schuell). The RNAs were bound covalently to the membrane by exposure to UV. The membranes were prehybridized with the Quick-Hyb buffer (Stratagene) for 20 min at 68° C., then hybridized for one hour at 68° C. with cDNA probes, labeled beforehand by random priming with $\alpha^{32}$P-dCTP (Amersham, 3000 Ci/mmol), then washed at room temperature in 2×SSC, 0.1% SDS (2×15 minutes), and at 60° C. in 0.1×SSC, 0.1% SDS (3×15 minutes). The Northern blot was quantified using a Phosphorimager (Molecular Dynamics) then exposed to autoradiographic films (Biomax MR; Kodak) at −80° C.

A cDNA of 1.4 kb cut by EcoRI and HindIII from the GAPDH gene (Fort et al., 1985) and one of 0.5 kb cut by EcoRI and HindIII from the HSS-26 gene (Vincent et al., 1993) were used as control probes. To analyze the encoding of the mRNAs of each isotype of tubulin (Lewis et al., 1985; Villasante et al., 1986; Wang et al., 1986), specific probes were generated from untranslated 3' sequences in the pUC vector by PCR using the pUC primers (5'-3' CTGCAAGGC-GATTAAGTTGG (SEQ ID NO: 15) and GTTGTGTG-GAATTGTGAGCG (SEQ ID NO: 16)).

The relative intensity of the bands was measured using a Phosphorimager (Molecular Dynamics). The mRNAs isolated from the brains of control animals at 2 days were used as reference and designated arbitrarily as 1. Exceptions were made for the mRNAs of tubulin α3/7 and β1 isolated from the testes and spleen of adult control mice, owing to absence of their expression in other tissues. The GAPDH values do not show any variation in expression between the values of the control animals and of the transgenic animals (Robert et al., 2001). In addition, for each Northern blot, correction factors that equalize the GAPDH values were calculated for normalizing the mRNA levels. The mean values of the various experiments at each postnatal stage were calculated and expressed as mean±standard error.

3. Isolation of Microtubules, Tubulin and Neurofilaments

The brains, spinal cords or sciatic nerves were dissected from adult mice, weighed and homogenized in RB buffer (mM MES, pH 6.8, 1 mM EGTA and 1 mM $MgCl_2$). The homogenates were centrifuged at 105 g at 4° C. for 1 hour in a Beckman LE-80k or TLX100 ultracentrifuge. For isolation of the microtubules, the first supernatant (S1) was incubated with 4M of glycerol and 0.1 mM of GTP at 37° C. for 1 hour, then centrifuged at 105 g at 37° C. to recover the polymerized microtubules and the neurofilaments in the second centrifugation deposit (P2).

The microtubules and the neurofilaments present in the deposit (P2) were suspended in RB buffer, incubated at 4° C. for 1 hour to depolymerize the microtubules and centrifuged at $10^5$ g at 4° C. for 1 hour. The unpolymerized tubulin fraction was recovered in the third supernatant (S3) by passing through a phosphocellulose column as described by Weingarten et al., 1975. For purification of the neurofilaments, a similar protocol was used, except that GTP was not added and all the stages were carried out at 4° C. to prevent polymerization to microtubule, as described previously by Leterrier and Eyer (1987).

4. Quantification of Proteins and Western Blot Analysis

The BCA assay kit (Pierce) was used for quantifying the proteins in each fraction. The proteins were separated subsequently with a 7.5% SDS-PAGE gel according to Laemmli (1970), and were revealed with Coomassie blue. Alternatively, the proteins separated in similar gels were transferred onto nitrocellulose membranes (Immobilon, Millipore). For immunodetection analyses (Towbin et al., 1979) the neurofilament subunits were identified using anti-NFH, anti-NFM and anti-NFL monoclonal antibodies (Sigma N5389, N5264, N5139), and an anti-NFH polyclonal antibody (Sigma N4142). The tubulin isotypes were identified using antibodies recognizing α-tubulin, β-tubulin, βIII-specifically neuronal tubulin, γ-tubulin (Sigma T9026, T4026, T8660) and polyglutamylated tubulin epitopes (GT335).

The experiments were carried out in triplicate and all the membranes were hybridized with each antibody, and dehybridized between each hybridization, in accordance with the supplier's instructions. Each reaction was detected using a chemiluminescent protocol (ECL, Amersham). To evaluate the intensity of the reaction, the exposed films were scanned and quantified by measuring the area and density of each spot with the ImageQuant software (Molecular Dynamics) or NIHImage. For each experiment, the signal of the control sample was used as reference.

5. Precipitation of Tubulin with the Neurofilaments

An equal amount of neurofilaments (40 µg) was incubated with different amounts of purified tubulin for 1 hour at 4° C. then centrifuged for 30 minutes at 100000 g at the same temperature. The supernatant and the resuspended deposits (in RB) were stored at −20° C. before Western blotting.

6. Peptide-on-Membrane Chips and Synthetic Peptides

Peptide chips corresponding to the NFL, NFM and NFH neurofilament subunits were obtained according to Frank et al., 1992, with an ASP 222 automat spot robot. Each neurofilament sequence was divided into sequences of 15 amino acids.

These peptides overlap 12 amino acids of the next peptide. The overlapping peptides were synthesized on spots, like a chip, on a specially produced cellulose membrane (AIMS scientific product, GmbH, Braunschweig, Germany). The peptides are bound to the membrane with a polyethylene glycol bridge owing to their carboxy-terminal amino acid. The synthetic procedure followed is that of Frank et al., 1996.

7. Blot Overlay Experiments

The proteins present in the third deposit (P3) of a typical preparation of microtubules (which is enriched with neurofilaments) were separated on a 7.5% SDS-Page gel, then transferred onto a nitrocellulose membrane, according to Towbin et al. (1979). The membranes were cut into strips, and blocked with TBS (1×) containing 10% of milk powder. These strips were incubated overnight at 4° C. with the purified tubulin. After extensive washing with TBS (1×) the membranes were immunolabeled with anti-$\beta$III-tubulin or anti-$\alpha$-tubulin antibodies in order to detect the proteins that interact with tubulin. The same membranes were then dehybridized and re-hybridized with new antibodies in order to confirm the nature of the strips that were recognized by reaction to tubulin and to anti-tubulin.

Alternatively, the strips that were detected were cut out and analyzed by mass spectrometry. The peptide-on-membrane chip was incubated overnight at 4° C. with purified tubulin. After extensive washing with TBS (1×) the membranes were incubated with anti-$\beta$III-tubulin antibodies in order to detect the amino acid sequences that interact with tubulin.

8. Spectrophotometric Analysis of Microtubule Polymerization

The polymerization of tubulin from the supernatant S3 of a microtubule preparation was investigated by turbidimetry. Briefly, the supernatant S3 (3 mg/ml) was incubated at 37° C. in the presence of 1 mM of GTP in a Helios $\alpha$ thermospectronic spectrophotometer to monitor the variations in optical density at 350 nm.

9. Immunohistochemical Analyses by Confocal Microscopy

The mice were sacrificed by injection of a lethal dose of anesthetic with avertin (8 mg/kg), then transcardiac perfusion was carried out, first with 50 ml of phosphate buffer to remove the blood, followed by 50 ml of 4% paraformaldehyde in phosphate buffer.

The samples were recovered, post-fixed in the same fixing buffer for one hour, then transferred to a 30% sucrose solution before being frozen in isopentane at −40° C. and stored at −80° C. Cryostat sections (10 μm) were prepared, placed on slides and stored at −80° C. for immunohistochemical analyses. The slides were brought back to room temperature and rinsed 3 times with phosphate buffer before being blocked at room temperature for 2 hours with 5% bovine serum albumin (BSA) for the anti-neurofilament antibodies, or 5% BSA plus 5% goat serum for the anti-tubulin antibodies. The sections were rinsed three times, 5 minutes each with phosphate buffer and incubated overnight with the primary antibodies (in 1% phosphate buffer BSA).

The sections were then rinsed three times 5 minutes each and incubated with fluorescent secondary antibodies (Alexa 488 nm anti-mouse antibodies, and Alexa 568 nm anti-rabbit antibodies from Molecular Probes, diluted to 1/200). Each antibody was incubated consecutively for an hour and a half then rinsed three times for 5 minutes.

The slides were fixed with an anti-ageing medium and stored at 4° C. in the dark before observation. The primary antibodies and the dilutions used were as follows: the anti-$\alpha$-tubulin, anti-$\beta$-tubulin and anti-$\beta$III-tubulin monoclonal antibodies were diluted to 1:100; the anti-NFH and anti-peripherin polyclonal antibodies were diluted to 1:1000 and 1/100 respectively. The immunolabeled slides were analyzed with an Olympus confocal microscope (BX50) using the Olympus Fluoview 3.0 software.

10. Electron Microscopy and Quantification

Analysis by electron microscope was carried out according to the protocols described previously (Eyer and Peterson, 1994). The density of the axonal microtubules was evaluated by scanning the negatives of electron micrographs (taken at 25000× using a JEOL JEM2010 electron microscope) of axons selected at random from each genotype using a U-MAX/ASTRA2400S scanner. The images were imported to an 8600 PowerPC/Macintosh computer using Photoshop. The microtubule density was evaluated by counting the number of microtubules/hexagon as described by De Waegh et al., 1992.

III Results

1. The Unpolymerized Tubulin is Co-Isolated with the Neurofilaments (FIG. 1)

Neurofilaments are isolated from brains and spinal cords of normal mice by conventional biochemical procedures.

Initial purification involves addition of glycerol 4M final to the supernatant (S1) obtained from the raw homogenate.

When these mixtures are incubated for one hour at a temperature of 4° C., the neurofilaments form a gel which is deposited in the second centrifugation residue (P2) (Leterrier and Eyer, 1987).

When the incubation/centrifugation stage is repeated with residue P2, other neurofilaments can be recovered in residue P3. Strangely, Western blotting of fractions enriched with neurofilaments detects the presence of tubulin species of both $\alpha$ and $\beta$ just as much as $\gamma$. Similar results were obtained when the supernatants were incubated with colchicine (up to 3 mM), which prevents microtubule assembly, or after multiple cycles of sedimentation and resuspension of the deposits at low temperature, a condition which also prevents microtubule assembly (FIG. 1A).

Figure 1B:
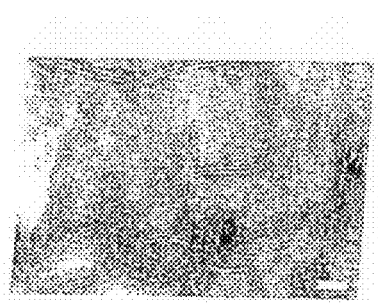

Examination of the neurofilaments recovered in the P3 fractions by electron microscopy detected an abundance of neurofilaments highly decorated by amorphous material. In contrast, microtubules were rare in these fractions and when they were found they were short. Typically, when 10 μg of the P3 fraction was loaded at a temperature of 4° C. on a grid of 300 mesh, only a few rare grid squares contained short microtubules. However, when these same fractions were incubated at 37° C. in the presence of 1 mM GTP, to promote polymerization, many long microtubules could be recognized in each grid square (up to 50) and were often associated with neurofilaments (FIG. 1B).

These observations show that unpolymerized tubulin (cold isolation) is associated with the neurofilaments. This tubulin conserves all its potential for polymerization in favorable conditions (37° C. in the presence of GTP).

In order to compare the relative amount of tubulin sedimenting as microtubules with that bound to the neurofilaments, as demonstrated by sedimentation in the neurofilament fraction, the raw brain sample (S1) was incubated in the presence of GTP and glycerol, either at 37° C. or at 4° C., prior to centrifugation at the same temperature.

After incubation at 37° C., 9.55±1.14% of the total proteins was recovered in the deposit whereas 90.45±1.14% remained in the supernatant.

After incubation at 4° C., 4.53±0.34% is present in the deposit whereas 95.43±0.34% remained in the supernatant (n=3).

It therefore appears that 5% of the total proteins contained in the raw sample (S1) represents unpolymerized tubulin that is capable, with associated proteins, of polymerizing to microtubules.

After evaluating the capacity of neurofilaments to bind tubulin, an identical amount of neurofilaments was incubated with increasing amounts of tubulin for one hour at 4° C., then centrifuged for 30 minutes at 100000 g.

Analysis by Western blotting of each deposit and of the supernatants was then carried out by Western blotting to determine their content of tubulin.

Figure 1C:
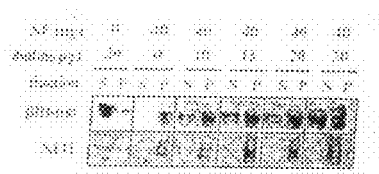
Figure 1C:
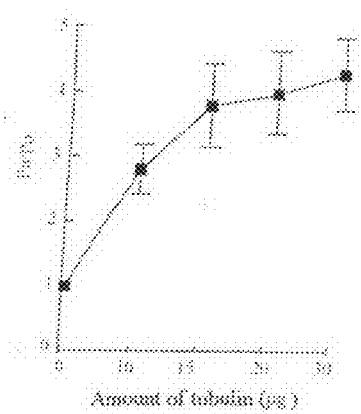

FIG. 1C shows that tubulin present in the deposit with the neurofilaments increased following saturable addition of exogenous tubulin, thus suggesting saturable interaction between the two partners.

Note that, without neurofilament, the amount of tubulin present in the deposit is much less than the amount of tubulin in the deposit without added exogenous tubulin.

2. Identification of Tubulin Binding Sequences on the Neurofilaments and Investigation of the Effect of the Sequences In Vitro (FIG. 1D, FIG. 2 and Table 1).

Figure 1D:
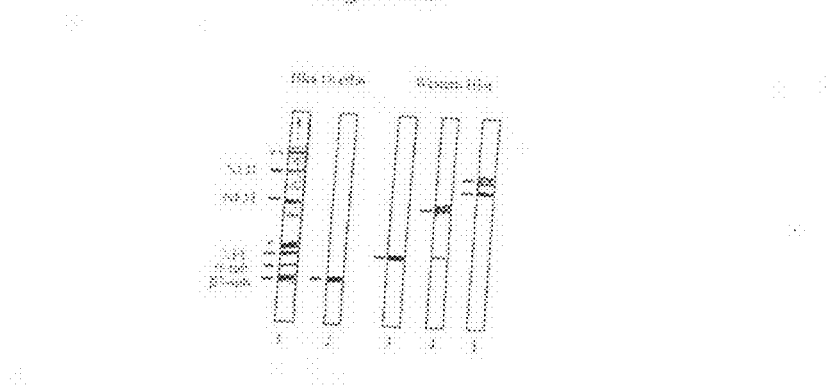

For further investigation of the molecular partners of this interaction, we carried out blot overlay experiments (FIG. 1D).

The third fraction of a preparation of neurofilaments (P3), which is enriched with neurofilaments, was separated on 7.5% SDS-PAGE gel, then transferred to a nitrocellulose membrane. The membrane was incubated with pure tubulin, then followed conventional Western blotting using anti-βIII-tubulin antibodies to identify the proteins that interact with the tubulin (FIG. 1D, line 1). This approach revealed direct interaction between tubulin and the three neurofilament subunits NFL (3), NFM (4), and NFH (5).

When no tubulin is added, the tubulin anti-βIII only recognizes one group, the tubulin βIII which is present in fraction P3 (2).

Taking into account the intensity of the signals, the interaction of tubulin is more intense with NFL and NFM than with NFH.

Moreover, only the phosphorylated isoform of NFH binds tubulin. Two additional signals were detected with this method and correspond to synapsin I and II and to the proteins MAPs.

However, synapsin was not co-purified with the neurofilaments and did not co-aggregate with the neurofilaments in the cell bodies of the NFHLacZ mice (data not communicated, see below).

Figure 2A:
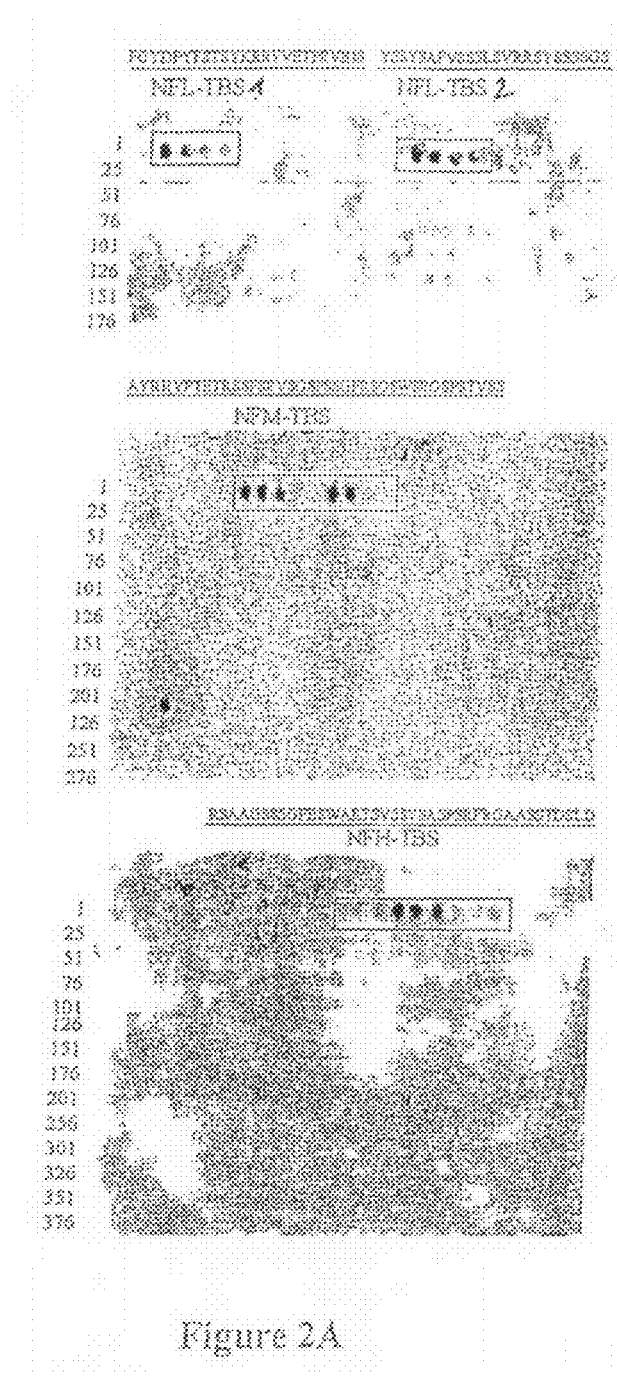

In order to identify the sequences responsible for the binding of tubulin to the neurofilaments, we use peptide-on-membrane chips, corresponding to the three neurofilament subunits (see experimental procedures). This method makes it possible to identify the binding domain involved in protein-protein interaction. The blot overlay experiment with purified tubulin on peptide chips revealed that the tubulin binding site is located in the N-terminal domain of the neurofilament sequences. The NFL subunit contains two tubulin binding sequences of 24 amino acids which we call NFL-TBS1 and NFL-TBS2 whereas NFM-TBS and NFH-TBS both contain 39 amino acids (FIG. 2A).

We showed previously in FIG. 1 that the neurofilaments contained unpolymerized tubulin. Taking this result into account, identification of the tubulin binding sites may have functional relevance in vitro for tubulin polymerization, i.e. may be capable of influencing the microtubule dynamics. To test this hypothesis, we conducted turbidimetry experiments with the various peptide sequences identified by blot overlay on the peptide chip. For this purpose, the supernatant S3 (containing free tubulin), obtained from a microtubule preparation, was polymerized at 37° C. in the presence of 1 mM GTP and several concentrations (3, 10, 30, and 100 µM) of tubulin binding peptide, which were added before polymerization (t=0). FIG. 2C, 1, 2, 3, 4 shows that each peptide has a dose-dependent inhibitory effect on microtubule formation.

Figure 2B:
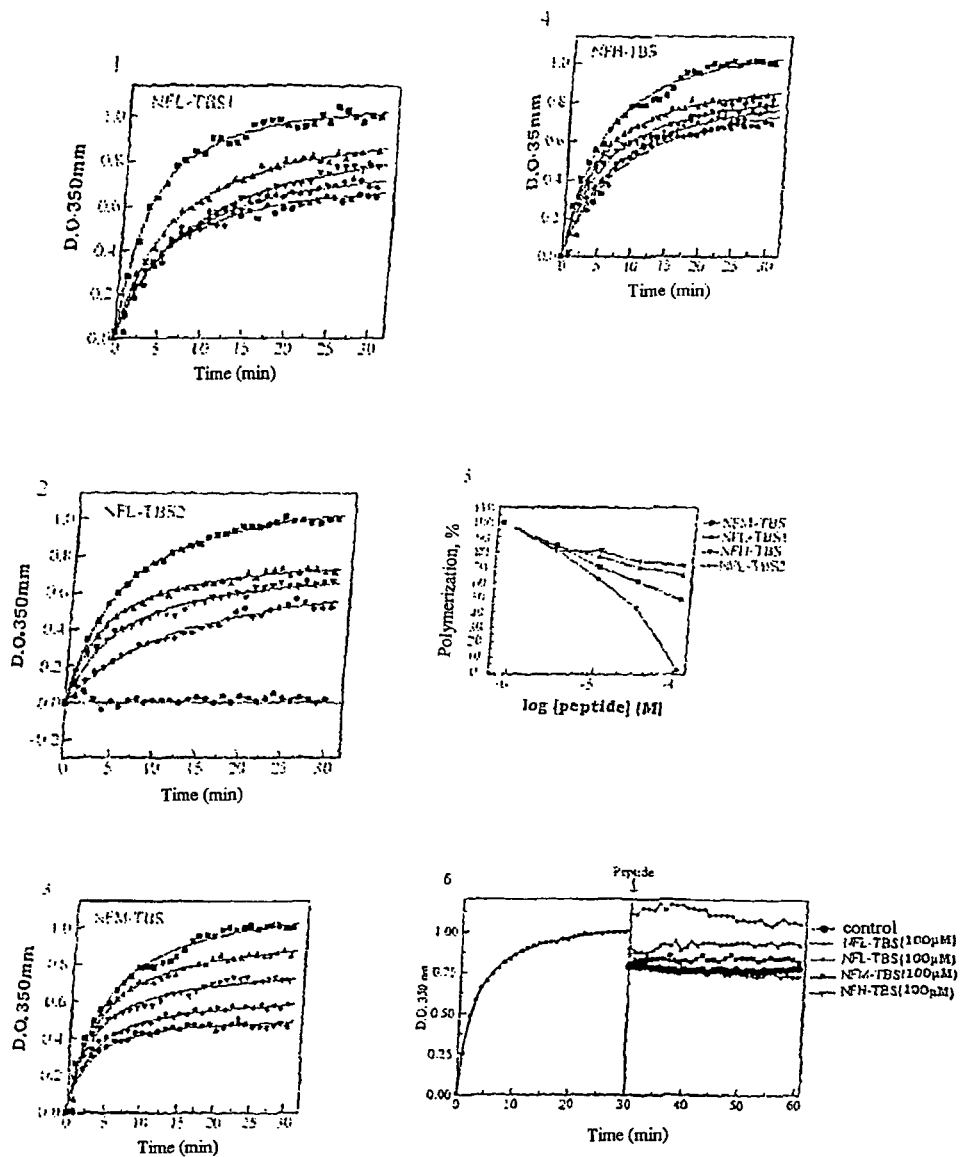

The inhibition capacity of the peptides was approximately 30% with a concentration of 100 µM except for NFL-TBS2 which gives 100% inhibition of tubulin polymerization at 100 µM (FIG. 2B 5). It appears that the process involved in this inhibition is specific to the mechanism of polymerization since these peptides have no effect on the preformed microtubules, at 30 minutes of polymerization (FIG. 2B 6).

Bioinformatic analyses on the N-terminal sequences of the neurofilaments show that the peptides tested below are located in a highly conserved zone of this domain if we consider the number of amino acids conserved between the three neurofilament subunits and between the species (BLAST). This conservation is specific to the N-terminal domain of the neurofilaments (Table 1) and appears to be lost or weaker when carrying out an alignment with other types of intermediate filaments.

TABLE 1

Analysis of homology between the sites involved in binding with tubulin
(SEQ ID NOS 41-48, 49, 50-52, respectively, in order of appearance)

```
             *         20         *         40         *         60         *         80
NFL: MSSFG-YDPYFS-TSYKRRYVETPRVHIS9VRSGYSTA-RSAYSSYSAPVSSSLSVRRSYSSS----SGSLMPSLEN-LD: 72

NFM: MS-YT-LDSLGNPSAYRRVPTET-RSSFSRVSGSPSSGFRSQSWSRGSPSIVSSSYTRSAVAPRLAYSSAMLSSAESSLD: 77

NFH: MS-FGSADALLG-APFAPLHGGG-SLHYSLSRKAGPGGTRSAAGSSSGFHSWARTSVSSVSASPSRFR-GAASSTDS-LD: 7T

*             20          *          40          *         60         *          80          *          100
NFL: MSSFGYDPYF---------STSYKRRYVETPRVHISSVRSGYSTARSAYSSYSAPVSSSLSVR--RSYSSSGS------------
     ---------LMPSLRNLD-VS: 74

NFM: MSYTLDSLGNP----------SAYRRVPTETR--SSFSRVSGSPSSGFRSQSW----SRGSPSTVSSSYTRSAVAPRLAYSSAM---
     ---------LSSARSSLD-FS: 79

NFH: MSFGSADALLG----------APFAPLHGGGS-LHYSL-SRKAGPGGTRSAAG-SSSGFHSWARTSVSSVSAS-PSRFRGAA-----
     ---------SSTDSLDTLS: 78
```

TABLE 1-continued

Analysis of homology between the sites involved in binding with tubulin
(SEQ ID NOS 41-48, 49, 50-52, respectively, in order of appearance)

```
Desmin: SQAYSSSQR--------VS--SYRRTFGGAPGF-SLG--FPLSSPVFPRAGFGTKGSSSS---MTSRVYQVSRTSGGAGGLGSL
RSSRLGTTRAPSYGAGELLD-FS: 91

Vimentin: MSTRS-------------VSSSSYRRMFGGSGT-SSRP-SSNRSYVTTSTRTYSL-GSALR---PSTSRSLYSSSPGGAYVT
RSSAV-RLRSSVPGVRLLQDSVD-FS: 87

Keratin-8: MSTR--------------VTQKSYKMSTSGPRAFSSRSFTSGPARISSS-SFSRVGSSSSSFRG-SMGTG---VGLGGFGG
AGVGGITAVTVNQSLLSP--------: 81

EndoA: MSIR--------------VTQKSYKMSTSGPRAFSSRSFTSGPGARISSS-SFSRVGSSSSSFRG-SMGTG---VGLGGFGGAGV
GGITAVTVNQSLLSP--------: 81

GFAP: MERRRI----------------TSAKRSY-----ASETVVR-------------GLGPSRQLGTMPR--FSLSRMTPP---------
-------------LPARVD-FS: 50

Peripherin: MPSSASMSHHHSSGLRSSISSTSYRRTFGPPPSLSPGAF--------SYS-SSSRFSSSRLLGSG-SP-SSS-ARLGSFR
APRAGALRL---------PSERLD-FS: 85 a-internexin: MSFGSEHYL---------CSASSYRKVFGDSSRLSARLSGPGGSGSFRSQ-SLSR--SNVASTAACSSASS---LGLG
LAYRRLP--------------ASDGLD-LS: 78
```

The sequence of the three subunits of the neurofilaments and of various intermediate filaments were aligned with the program ClustalW depending on their homology (endoA: cytokeratin endoA; Ker 8: keratin 8; NFL: light neurofilament subunit; NFM: medium neurofilament subunit; NFH: heavy neurofilament subunit; periph: peripherin; internex: α-internexin; GFAP: glial filament; vim: vimentin).

A large number of amino acids are conserved in the N-terminal portion of the three subunits of the neurofilaments and to a smaller extent in the N-terminal domains of the other intermediate filaments.

3. Morphometric Analysis of the Axonal Microtubule Cytoskeleton in NFHlacZ Transgenic Mice (FIG. 3)

For in vivo investigation of the significance of the neurofilament-tubulin association demonstrated in the above biochemical studies, we investigated NFHlacZ transgenic mice, in which the distribution of the neurofilaments is disturbed.

Under the influence of NFH regulating elements, the NFHlacZ transgene is expressed in the majority of the neurons.

The fusion protein encoded by the transgene is assembled in the network of neurofilaments and, via the β-galactosidase dimerization domains, crosslinks the assembled neurofilaments, and prevents their export to the axonal compartment. Despite the bad distribution of the cytoskeleton of the neurofilaments, these neurons are generally viable up to an advanced age (Eyer and Peterson, 1994).

In order to determine whether the absence of neurofilaments in the axons of the NFHlacZ transgenic mice affects the microtubule cytoskeleton, samples from sciatic nerves and spinal cords obtained from elderly mice were examined by electron microscopy (FIG. 3). A characteristic, dense network of neurofilaments was observed in the sections of all the axons of large diameter obtained from normal sciatic nerves.

In the transgenic samples, few if any neurofilaments could be recognized, whereas in contrast, the axonal microtubule cytoskeleton was particularly dense.

To evaluate microtubule density, the microtubule profiles found within a predetermined area of section were computed (De Waegh et al., 1992). The control axons contained $9.44 \pm 1.4$ microtubules/$\mu m^2$ whereas in the same axonal zone in the transgenic samples (number of axons=500), the microtubule density was more than 10 times greater at $99.06 \pm 5.1$ microtubules/$\mu m^2$.

It had been shown previously that the mean diameter of the axons in the NFHlacZ transgenic mice was reduced by 50% (Eyer and Peterson, 1994). Therefore the high microtubule density in the axons might merely be a consequence of the decrease in axonal volume. However, the volume changes alone are not sufficient to explain the extent of the observed increase in tubule density, that is, if we assume a circular profile, a normal axon having a diameter of 10 μm with a section area of 78.5 $\mu m^2$, and at $9.44 \pm 1.4$ microtubules/$\mu m^2$, would have to contain about 741 microtubule profiles.

If the same axon was deficient in neurofilaments, its diameter would be reduced to 5 μm and would have a section area of 19.6 $\mu m^2$. If the same number of microtubules were present, their density would be 741/19.6 $\mu m^2$ or 37.8 microtubules/$\mu m^2$.

Therefore a maximum density increase of four times (37.8/9.44=4.0) might be due to the 50% reduction in axonal caliber alone. Consequently, the transgenic samples contain two-and-a-half times more microtubules than would be predicted from just the parameters of volume and concentration, since the microtubule density is increased ten-fold.

4. Accumulation of Tubulin mRNA, Expression Profile and Distribution of Isotypes (FIG. 4 and FIG. 5 and Table 2)

Axonal development as well as regeneration are associated with a complex program of expression of tubulin isotypes regulated temporally and spatially, often reflecting the density of the microtubule networks. We determined whether the tubulin mRNAs varied in samples from normal or transgenic mice of increasing age. Despite an exhaustive evaluation of the accumulation of mRNAs, no obvious difference was observed during postnatal development of the animals.

Figure 4A:
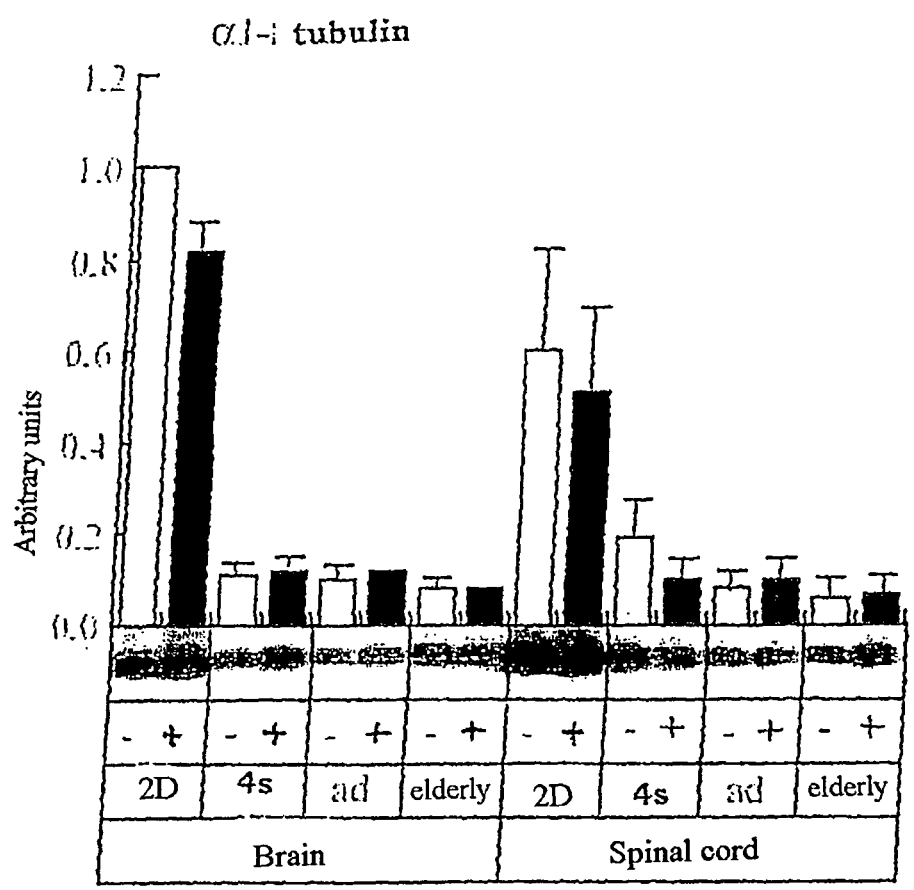
Figure 5A:
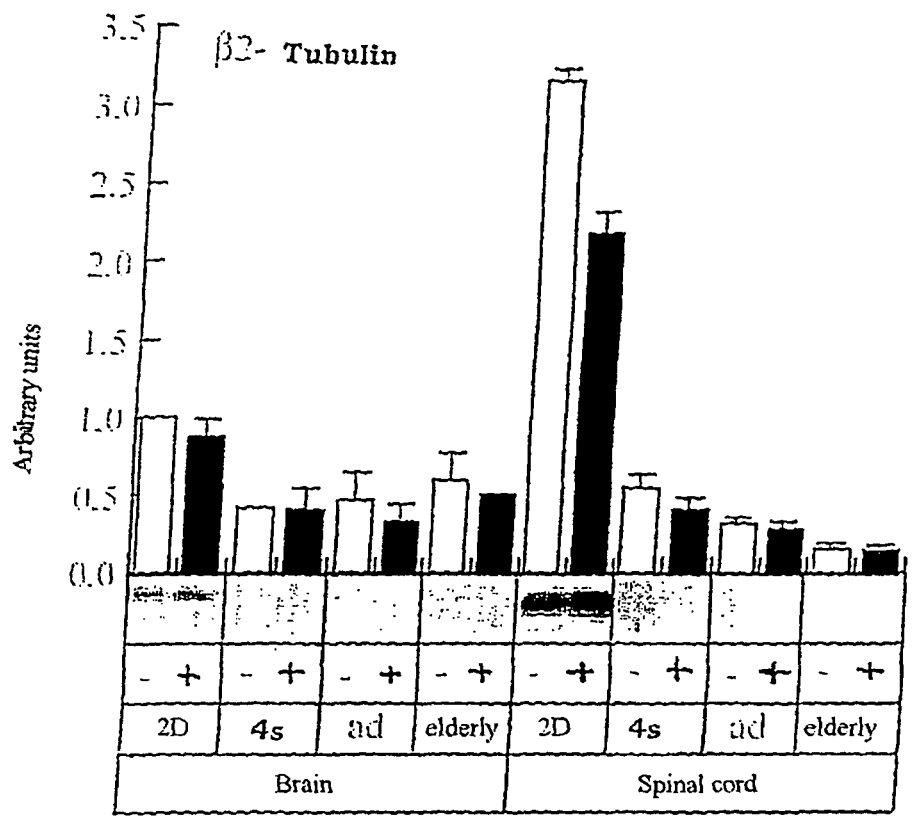

Analysis by Northern blot of control brains and of samples of spinal cords obtained during the first month of growth ex-utero revealed a definite decline for the mRNAs of the two tubulin isotypes Mα1 and Mβ2. This was followed by a low level being maintained throughout maturity (FIGS. 4A, 5A).

Figure 4B:
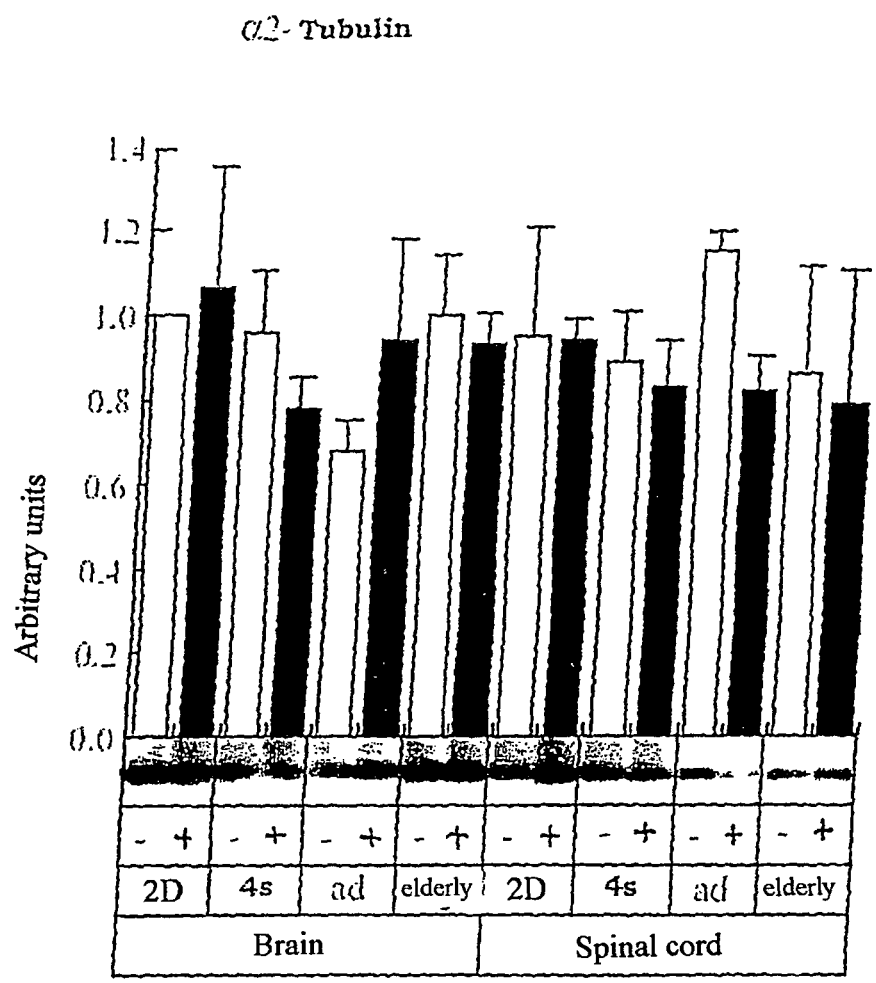
Figure 5B:
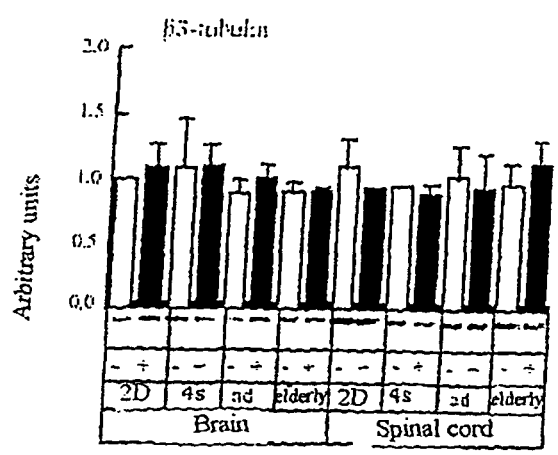

The expression profiles of the mRNAs Mα2 and Mβ3 are similar between the brain samples and the spinal cord samples, both being present at a high level at birth and remaining high throughout maturity (FIGS. 4B and 5B).

For each Northern blot, the signals were normalized by GADPH which was not changed by aggregation of the NFs (Robert et al., 2001). The signal obtained at two days serves as a reference and is fixed at 1 except for tubulin β5 2.8 kb(*), which is compared with the signal from tubulin 1.8 kb at 2 days in the control brain (ND: not determined, because the signal was too weak).

Figure 5C:
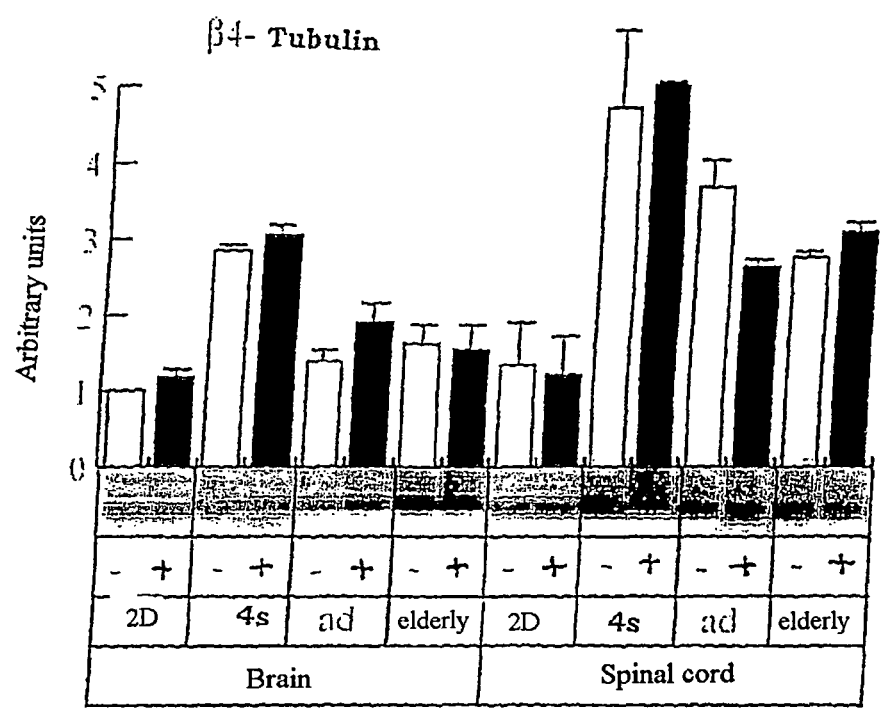
Figure 5D:
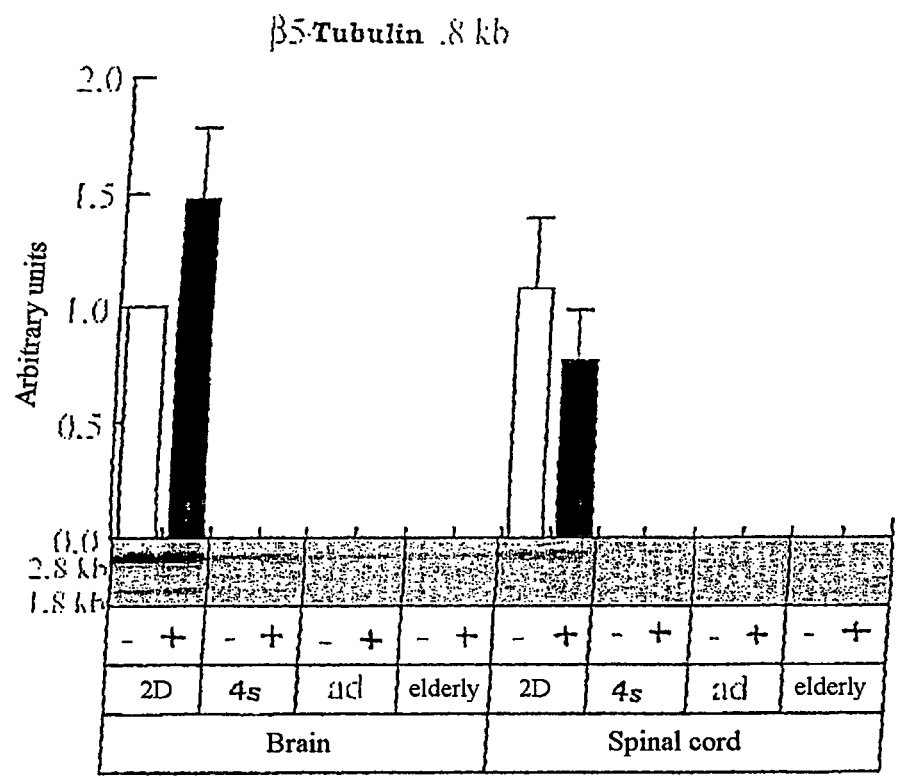
Figure 5E:
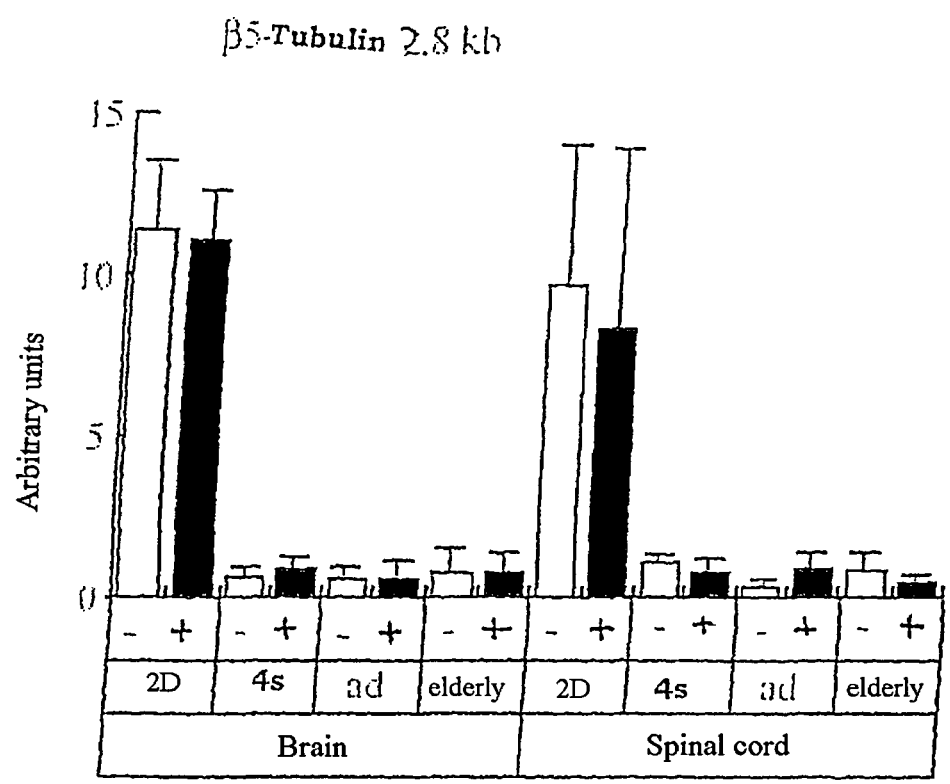

We detected a two-phase profile for the expression scheme of the mRNAs of tubulin Mβ4 in the samples of brain and spinal cord (FIG. 5C).

The untranslated 3' sequence of Mβ5 recognized two transcripts of 1.8 and 2.8 kb (FIG. 5D, 5E), which also underwent a strong decline between the second day post partum and maturity at four weeks.

Figure 4C:
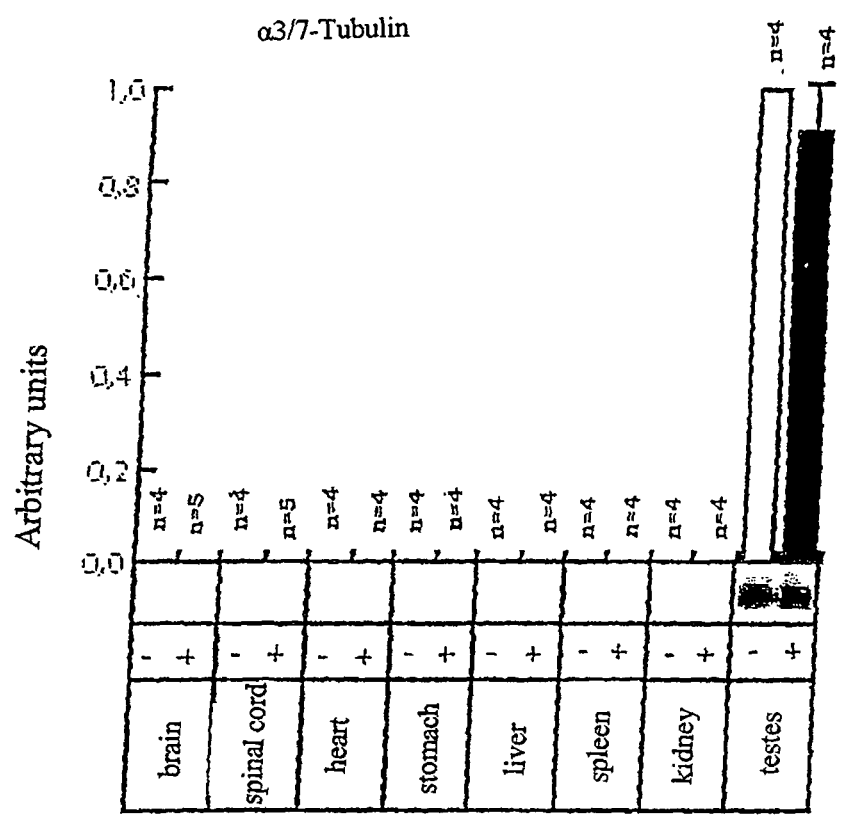
Figure 5F:
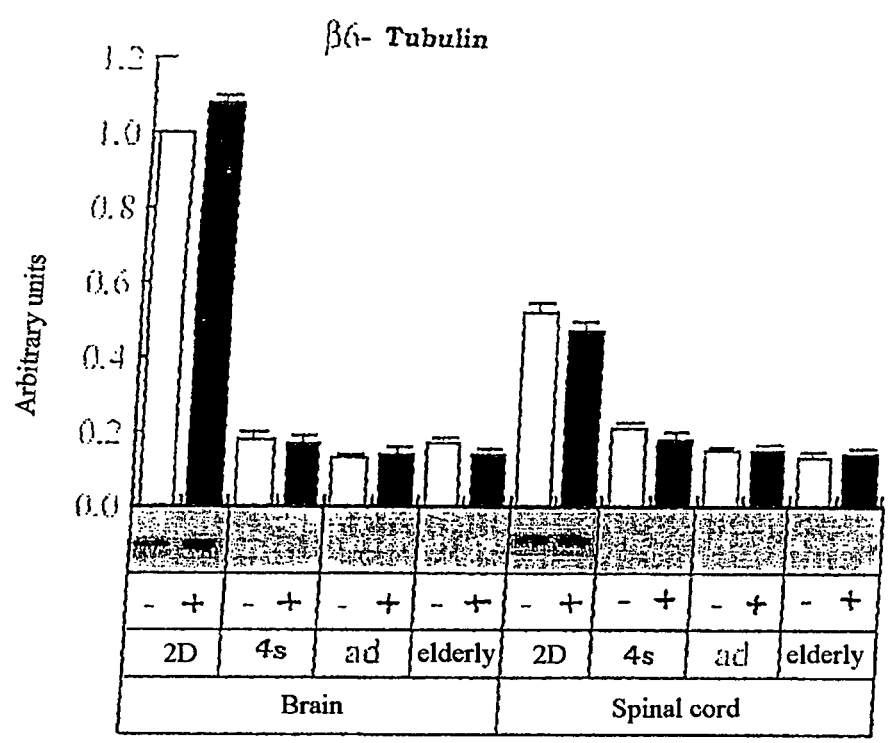

Finally, the expression profile of tubulin Mβ6 is quite similar to that observed for tubulin Mα1 (FIGS. 5F and 4A). No indication of the expression of deregulated isoforms was detected in the transgenic mice. For Mα3/7, normally expressed in the testes (Villasante et al., 1986) and Mβ1, normally hematopoietic-specific (Wang et al., 1986), no signal was detected in the samples from brain and spinal cord, at any stage of development (FIG. 4C).

For the tubulin isotypes tested in this study, no difference was observed in the expression profiles of the mRNAs between the transgenic and control samples, thus suggesting that changes in axonal microtubule density are effected at the post-translational level.

TABLE 2B

The amount of tubulin proteins is not altered in the transgenic mice

| B | +/−ratio (%) | | |
|---|---|---|---|
| | BRAIN | SPINAL CORD | SCIATIC NERVE |
| α-tub | 97 ± 3 | 105 ± 8 | 97 ± 5 |
| β-tub | 103 ± 30 | 106 ± 26 | 105 ± 10 |
| βIII-tub | 99 ± 7 | 119 ± 21 | 91 ± 9 |
| GT335 | 104 ± 2 | 126 ± 33 | 94 ± 12 |

The signals obtained for the control mice were fixed at 100% and the control/transgenic ratios were calculated for each experiment. No difference in amount of tubulin was observed between the control and transgenic mice.

In order to determine whether the increase in the number of axonal microtubules may be due to an increase in tubulin polymerization efficiency, we investigated the relative polymerizability of tubulin from brains of transgenic or control animals. For this purpose, the microtubule proteins were isolated by cycles of polymerization, at 37° C., and depolymerization at 4° C. (Weingarten et al., 1975). In each cycle, an

TABLE 2A

The amount of tubulin mRNA is unchanged in the transgenic mice.

| | 2 Days | | 4 Weeks | | Adults | | 18 Months | |
|---|---|---|---|---|---|---|---|---|
| A | − | + | − | + | − | + | − | + |
| | BRAIN | | | | | | | |
| α1 tubulin | 1 ± 0 | 0.82 ± 0.05 | 0.11 ± 0.03 | 0.12 ± 0.4 | 0.1 ± 0.01 | 0.12 ± 0.04 | 0.8 ± 0.01 | 0.08 ± 0.01 |
| α2 tubulin | 1 ± 0 | 1.06 ± 0.3 | 0.96 ± 0.18 | 0.78 ± 0.07 | 0.68 ± 0.07 | 0.94 ± 0.26 | 1 ± 0.17 | 0.93 ± 0.07 |
| β2 tubulin | 1 ± 0 | 0.88 ± 0.9 | 0.42 ± 0.0 | 0.41 ± 0.16 | 0.47 ± 0.18 | 0.33 ± 0.1 | 0.6 ± 0.22 | 0.5 ± 0.03 |
| β3 tubulin | 1 ± 0 | 1.09 ± 0.11 | 1.08 ± 0.32 | 1.1 ± 0.11 | 0.89 ± 0.07 | 1.01 ± 0.13 | 0.9 ± 0.09 | 0.9 ± 0.03 |
| β4 tubulin | 1 ± 0 | 1.19 ± 0.08 | 2.84 ± 0.08 | 3.07 ± 0.05 | 1.39 ± 0.1 | 1.89 ± 0.33 | 1.61 ± 0.24 | 1.55 ± 0.34 |
| β5 tubulin 1.8 kb | 1 ± 0 | 1.47 ± 0.35 | | | | | | |
| β5 tubulin 2.8 kb | 11.35 ± 2.93* | 11.04 ± 2.34 | 0.66 ± 0.11 | 0.92 ± 0.31 | 0.61 ± 0.21 | 0.59 ± 0.48 | 0.79 ± 0.54 | 0.75 ± 0.54 |
| β6 tubulin | 1 ± 0 | 1.08 ± 0.05 | 0.18 ± 0.04 | 0.17 ± 0.07 | 0.13 ± 0.02 | 0.14 ± 0.02 | 0.17 ± 0.02 | 0.14 ± 0.02 |
| | SPINAL CORD | | | | | | | |
| α1 tubulin | 0.6 ± 0.24 | 0.51 ± 0.19 | 0.19 ± 0.09 | 0.1 ± 0.05 | 0.08 ± 0.04 | 0.1 ± 0.05 | 0.6 ± 0.05 | 0.7 ± 0.04 |
| α2 tubulin | 0.95 ± 0.31 | 0.94 ± 0.06 | 0.89 ± 0.16 | 0.83 ± 0.15 | 1.15 ± 0.06 | 0.82 ± 0.12 | 0.86 ± 0.24 | 0.79 ± 0.31 |
| β2 tubulin | 3.15 ± 0.1 | 2.19 ± 0.2 | 0.55 ± 0.14 | 0.4 ± 0.11 | 0.31 ± 0.01 | 0.28 ± 0.03 | 0.15 ± 0.03 | 0.14 ± 0.02 |
| β3 tubulin | 1.1 ± 0.18 | 0.93 ± 0.0 | 0.95 ± 0.0 | 0.89 ± 0.05 | 1.02 ± 0.2 | 0.94 ± 0.24 | 0.96 ± 0.2 | 1.13 ± 0.18 |
| β4 tubulin | 1.33 ± 0.62 | 1.2 ± 0.37 | 4.73 ± 0.98 | 5 ± 0.04 | 3.7 ± 0.44 | 2.65 ± 0.04 | 2.77 ± 0.07 | 3.12 ± 0.25 |
| β5 tubulin 1.8 kb | 1.08 ± 0.38 | 0.77 ± 0.23 | | | | | | |
| β5 tubulin 2.8 kb | 9.64 ± 4.13 | 8.3 ± 6 | 1.12 ± 0.13 | 0.75 ± 0.62 | 0.35 ± 0.2 | 0.87 ± 0.62 | 0.85 ± 0.68 | 0.42 ± 0.24 |
| β6 tubulin | 0.52 ± 0.1 | 0.47 ± 0.08 | 0.21 ± 0.08 | 0.18 ± 0.05 | 0.15 ± 0.06 | 0.15 ± 0.06 | 0.13 ± 0.05 | 0.14 ± 0.08 |

5. Analysis of Accumulation of Microtubules and Capacity for Polymerization (FIG. 6, Tables 2A and 2C)

Figure 6A:
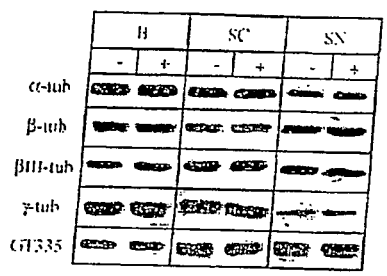
Figure 6B:
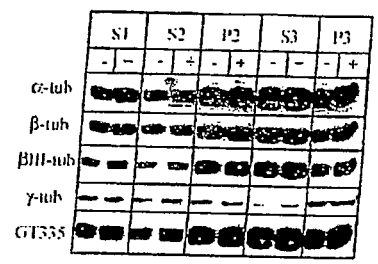

To evaluate the total amount of tubulin accumulated, raw homogenates of brains, spinal cords and sciatic nerves were analyzed by Western blot using antibodies recognizing tubulin α and β, the neuronal isoforms βIII, the polyglutamylated form GT335, and tubulin γ. To compare the relative accumulation of the isotypes, all the samples were prepared on the same gel and the same transfer membrane was analyzed sequentially, with all the antibodies. In each case, the binding antibodies were detected using a chemiluminescent reaction and the relative amount of tubulin between samples was determined by measuring the intensities of the signals on the film. The results of the experiments in triplicate (3 independent assays from samples prepared from two adult mice of each genotype) showed convincingly that the transgenic and control samples contain the same levels of each tubulin isoform investigated (FIG. 6A, Table 2B).

aliquot is taken and analyzed by Western blot, using the complete panel of anti-tubulin antibodies previously described, and by electron microscopy. Firstly, the supernatant of the raw extract (S1) was incubated at 37° C. and the assembled microtubules were recovered by sedimentation (P2). The assembled microtubules present in the second deposit were resuspended and then depolymerized at 4° C. before being centrifuged to obtain the free tubulin (S3) and "low-temperature-stable microtubules" (P3). No obvious quantitative difference was observed between the transgenic and control samples in any stage of this conventional procedure for microtubule purification (FIG. 6B).

When the same amount of proteins was deposited per well in the SDS-PAGE gel, and the ratio of the signal for the immunoreactivity of tubulin was evaluated (S2/P2 and S3/P3), the same values were obtained between the transgenic and control samples (Table 2C).

TABLE 2C

The ratios of polymerized to unpolymerized tubulin are not altered in the brain of the NFHLacZ mice.

| C | BRAIN | | | |
|---|---|---|---|---|
| | S2−/P2− | S2+/P2+ | S3−/P3− | S3+/P3+ |
| α-tub | 0.68 ± 0.27 | 0.61 ± 0.20 | 1.22 ± 0.27 | 1.29 ± 0.19 |
| β-tub | 0.83 ± 0.16 | 0.79 ± 0.11 | 1.29 ± 0.27 | 1.12 ± 0.20 |
| βIII-tub | 0.38 ± 0.05 | 0.39 ± 0.02 | 1.60 ± 0.68 | 1.49 ± 0.32 |

The same ratios S2/P2 were also obtained from sciatic nerves of transgenic or control mice (Table 2D).

TABLE 2D

The ratios of polymerized to unpolymerized tubulin are not altered in the sciatic nerve of the NFHLacZ mice.

| D | SCIATIC NERVE | |
|---|---|---|
| | S2−/P2− | S2+/P2+ |
| α-tub | 1.38 ± 0.78 | 1.39 ± 0.65 |
| β-tub | 1.33 ± 0.10 | 1.36 ± 0.47 |
| βIII-tub | 1.80 ± 0.58 | 2.06 ± 0.43 |

Tables 2C and D: Western blot analysis of different fractions of a preparation of microtubules from brains (C) or sciatic nerves (D) using different antibodies directed against tubulins α, β, βIII. The signals obtained were scanned and the S2/P2 and S3/P3 ratios were calculated. No difference was observed for these ratios between the control (−) and NFHLacZ (+) mice.

The S3/P3 ratios could not be evaluated owing to the small amount of proteins present in these samples.

Figure 6C:
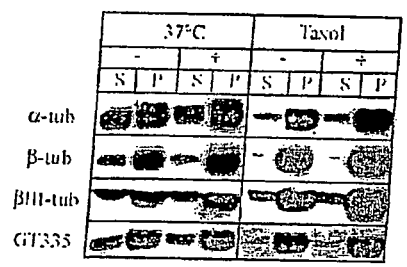
Figure 6D:
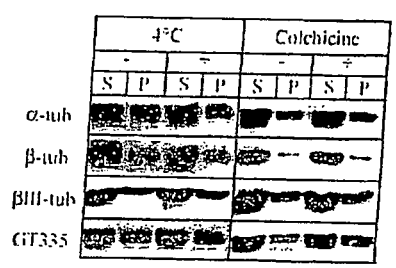

In addition, to compare the tubulin polymerization properties, raw extracts (S1) from transgenic or control brains were incubated under conditions permitting the formation of microtubules (37° C. or in the presence of Taxol (60 μM)). To evaluate the relative depolymerization potential, similar raw extracts were incubated in conditions that permit disassembly of the microtubules (4° C. or with colchicine). Following such treatments, each preparation was centrifuged and the microtubules were recovered from the deposit and the unpolymerized tubulin was recovered from the supernatant. Once again, no obvious difference in signal intensity was observed for the different tubulin epitopes in these samples from transgenic or control mice (FIG. 6C, D).

6. Ultrastructural and Immunocytochemical Analyses of Aggregates of Neurofilaments (FIG. 7)

Previous studies on NFHLacZ transgenic mice demonstrated that the neurofilaments are retained in dense aggregates within the cell body (Eyer and Peterson, 1994). To determine whether such aggregates of neurofilaments also exert an influence on microtubule assembly in vivo, we examined the aggregates for presence of tubulin and microtubules using both immunohistochemistry coupled with confocal microscopy, and electron microscopy. Although microtubule profiles are apparent in the cytoplasm adjacent to the aggregates, none was detected, either inside or at the periphery of the aggregates (the complete profiles of 50 aggregates were examined at 50,000×) (FIG. 7A). In contrast, in the immunocytochemical preparations evaluated by confocal microscopy, the tubulin epitopes were clearly detected inside the aggregates (FIG. 7B). Whereas the perikaryal aggregates were strongly labeled with anti-neurofilament and anti-peripherin antibodies, the strongest labeling for the tubulin epitopes was not observed inside the aggregates, but at the nuclear periphery and near the cytoplasmic membrane. Thus, whereas tubulin can be detected clearly inside the aggregates, it may be present at higher concentration in other subcellular compartments. In contrast to the heterogeneous distribution of the tubulin epitopes observed inside NFHLacZ neurons, homogeneous perikaryal labeling was observed in normal neurons, overlapping the signals obtained from anti-βIII-tubulin monoclonal antibodies and anti-NFH or anti-peripherin polyclonal antibodies (FIG. 7B). Similar distributions were also observed in transgenic and normal neurons for tubulin α, β and γ (not shown).

Example 2

The NFL-TBS2 Peptides Block Cell Division

The TBS peptides modify the in-situ assembly of microtubules, mitosis and cell proliferation.

The peptides of NFL-TBS2 exert a powerful effect on the in-vitro polymerization of tubulin. To determine whether they could also modify the in-situ assembly of microtubules, T98G cells were incubated with 10 μm of biotinylated peptides SEQ ID No. 6. After incubation for 6 hours, more than 75% of the cells contain the peptide (FIG. 8 A, A', A") and are characterized by an unusual spherical shape. Cells with a weak or absent signal measuring the presence of peptides maintained a normal microtubule cytoskeleton, but those containing the peptide SEQ ID No. 6 displayed a disunited network of microtubules with the tubulin and the peptides aggregated in an amorphous mass.

The microtubules constitute an important component of the achromatic spindle. To determine whether the presence of peptides SEQ ID No. 6 could affect cell division, the inventors usually carry out a FACS (Fluorescence Activated Cell Sorter) analysis to compare the distribution of the cycles of control cells and T98G cells treated with 10 μm of peptide SEQ ID No. 6.

After culture for 48 hours, 39% of the cells in the cultures not treated with the peptide SEQ ID No. 6 were in phase G1 of mitosis. Conversely, 61% of the cells in the cultures containing peptide SEQ ID No. 6 were in phase G1 of mitosis, thus suggesting stoppage of mitosis (FIG. 8 B, B').

The effect of exposure of peptide SEQ ID No. 6 on cell proliferation was confirmed using MTS analysis (described in Cory A. H. et al., 1991, Cancer Commun. 3, 207-212, incorporated here by reference) in which the inventors observed fewer cells in the cultures treated with peptide SEQ ID No. 6 (FIG. 8C).

In other experiments, media containing peptide SEQ ID No. 6 was replaced at 24 hours (to overcome any degradation of the peptide during incubation), and inhibition of the increase in number of cells in the stages following culture was also clearly observed (data not shown).

Thus, after this culture time, these results suggest that there is little (if any) degradation or elimination of peptide SEQ ID No. 6.

Similar results are observed using other cell lines, for example MCF7, LS187, Cos or NGP cells.

Example 3

Peptides of Other Intermediate Filaments Bind to Tubulin, Alter Microtubule Polymerization and Block Cell Division

Binding of Peptides from Other Intermediate Filaments to Tubulin

For directly testing whether other intermediate filaments can bind tubulin, peptide chips corresponding to the desmin, vimentin, cytokeratin and GFAP sequences were prepared and evaluated as described in the Material and Method section (Peptide-on-membrane chip and synthetic peptides) in Example 1. Each of these intermediate filaments has several tubulin binding sites:

- 3 peptides were identified for the protein desmin (FIG. 9A): Des-TBS1 (SEQ ID No. 17), Des-TBS2 (SEQ ID No. 18), and Des-TBS3 (SEQ ID No. 19).
- 3 peptides were identified for the protein vimentin (FIG. 9B): Vim-TBS1 (SEQ ID No. 20), Vim-TBS2 (SEQ ID No. 21), and Vim-TBS3 (SEQ ID No. 22)
- 3 peptides were identified for the protein cytokeratin (FIG. 9C): Ker-TBS1 (SEQ ID No. 23), Ker-TBS2 (SEQ ID No. 24), and Ker-TBS3 (SEQ ID No. 25)
- 3 peptides were identified for the protein GFAP (FIG. 9D): GFAP-TBS1 (SEQ ID No. 26), GFAP-TBS2 (SEQ ID No. 27), and GFAP-TBS3 (SEQ ID No. 28).

Effect of Peptides from Other Intermediate Filaments on Polymerization of the Microtubules As previously for the NF-TBS peptides, studies of the influence of the peptides of vimentin, cytokeratin and GFAP identified by peptide chip on the assembly of microtubules in vitro were carried out by the same technique as described previously in the Material and Method section (Spectrophotometric analysis of microtubule polymerization) in Example 1.

The results obtained for the peptides Vim-TBS3 (SEQ ID No. 22), GFAP-TBS3 (SEQ ID No. 28), Ker-TBS1 (SEQ ID No. 23), Vim-TBS2 (SEQ ID No. 21) and GFAP-TBS1 (SEQ ID No. 26) are shown in FIGS. 10A to 10E.

Figure 10A:
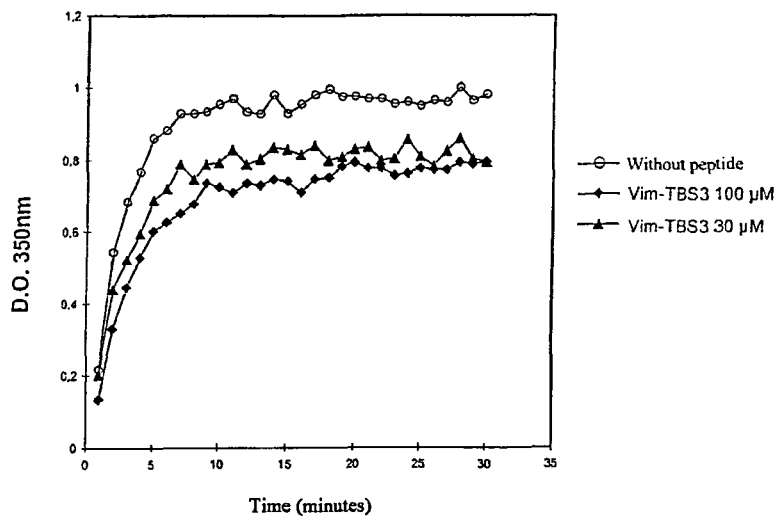
Figure 10B:
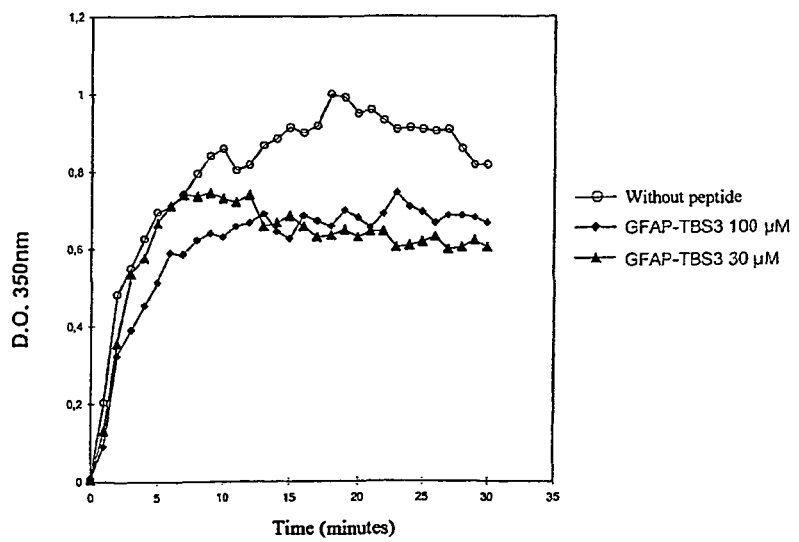

The results show that the peptides Vim-TBS3 (SEQ ID No. 22) and GFAP-TBS3 (SEQ ID No. 28), like the peptide NFL-TBS2 (SEQ ID No. 6), are inhibitors of microtubule polymerization (FIGS. 10A and B).

Figure 10C:
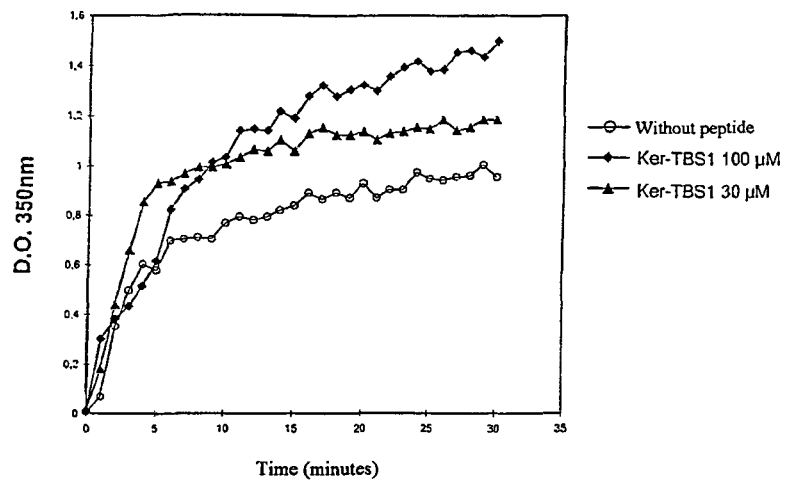
Figure 10D:
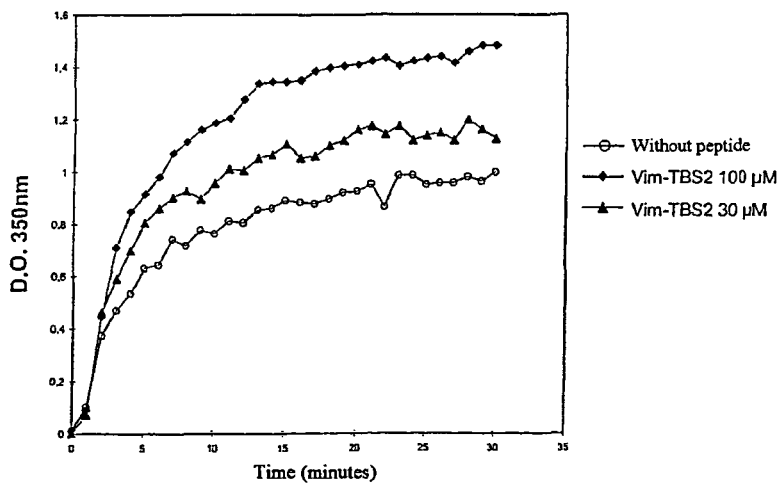
Figure 10E:
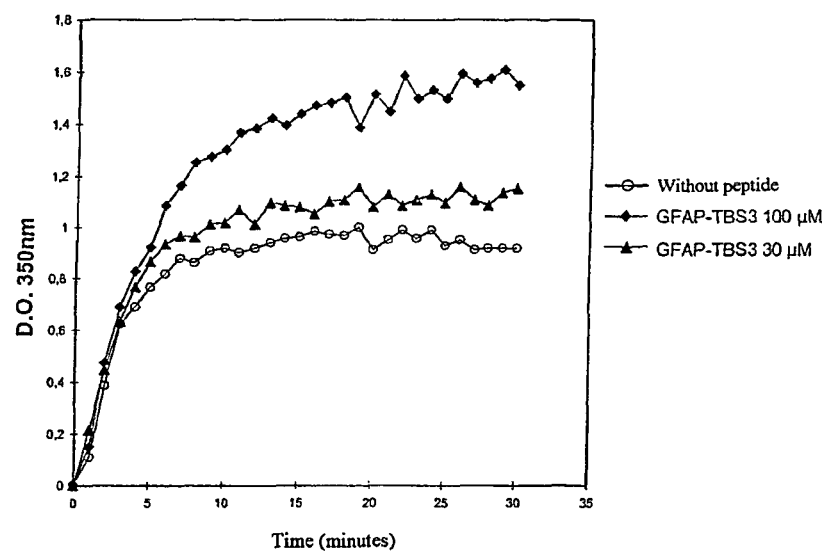
Figure 11:
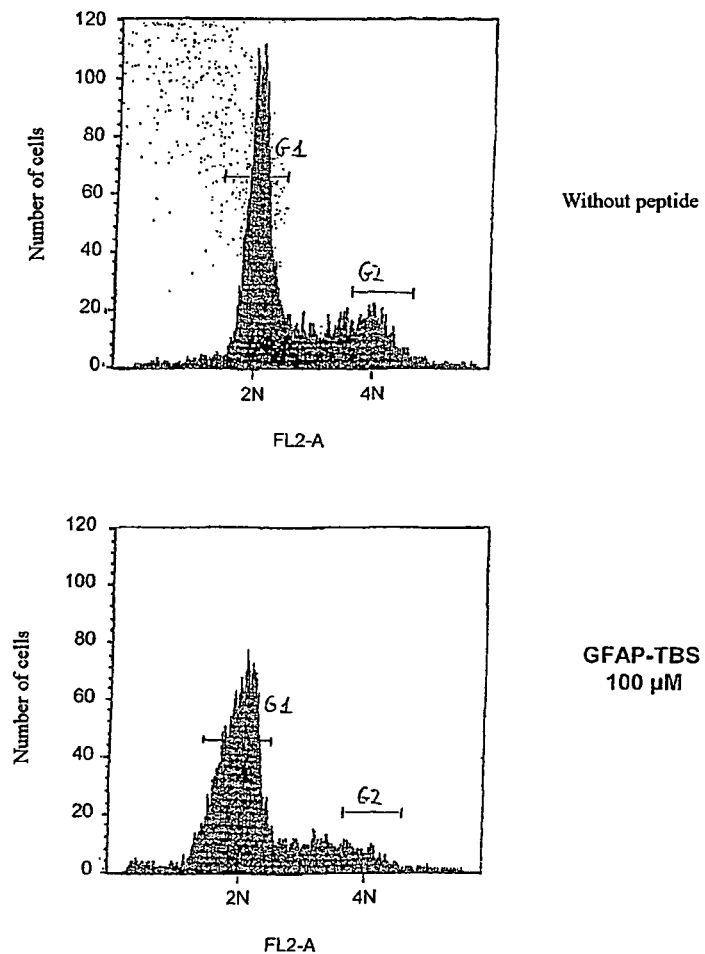

In contrast, peptides Ker-TBS1 (SEQ ID No. 23), Vim-TBS2 (SEQ ID No. 21) and GFAP-TBS1 (SEQ ID No. 26) activate microtubule polymerization (FIGS. 10C, D and E).

Effect of the Peptide GFAP-TBS1 (SEQ ID No. 26) on Cell Division

In order to determine how a peptide that is an activator of microtubule polymerization affects cell division, a FACS analysis was carried out to compare the distribution of the cycles of untreated T98G cells (without peptide) or treated with 100 μm of peptide GFAP-TBS1 (SEQ ID No. 26), by the same protocol as that described in Example 2.

As in Example 2 with peptide NFL-TBS2 (SEQ ID No. 6), in the presence of peptide GFAP-TBS1 (SEQ ID No. 26) we observe a decrease in the number of cells in phase G2 and an increase in the number of cells in phase G1 or sub-G1, indicating that the presence of the peptide GFAP-TBS1 (SEQ ID No. 26) inhibits cell division.

Thus, these results strongly suggest that peptides derived from intermediate filaments that bind to tubulin are capable of altering microtubule polymerization (inhibition or activation), and therefore, by some mechanism or other, block cell division.

In conclusion, the relations defined here between fragments of intermediate filaments and tubulin may illustrate a mechanism that is widely employed in regulation of microtubules.

The units corresponding to NF-TBS were studied in particular here and several of the latter are mutated in various human diseases such as amyotrophic lateral sclerosis, or in skin diseases, for which the various mutations are listed on the website www.interfil.org. Moreover, many of these TBS-binding residues are subject to phosphorylation that is dependent on the cell cycles, suggesting their possible involvement in tubulin binding/release equilibria (Chou et al., 1996; Goto et al., 1998; Ku et al., 1998; Toivola et al., 2002; Chou et al., 2003).

The results also show that fragments of other intermediate filaments (desmin, vimentin, cytokeratin and GFAP) also possess fragments capable of binding to tubulin, altering polymerization of the microtubules (inhibition or activation) and blocking cell division, demonstrating the existence of an important, common mechanism of control of cell division by altering microtubule polymerization.

REFERENCES

Carden, M. J., Trojanowski, J. Q., Schlaepfer, W. W., and Lee, V. M. Y. (1987). Two stage expression of neurofilament polypeptides during rat neurogenesis with early establishment of adult phosphorylation patterns. J. Neurosci. 7, 3489-3504.

Cassimeris, L. (2002). The oncoprotein 18/stathmin family of microtubule destabilizers. Curr. Opin. Cell Biol. 14, 18-24.

Chomczynski, P., and Sacchi, N. (1987). Single-step method of RNA isolation by acid guanidinium thiocyanate-phenol-chloroform extraction. Anal. Biochem. 162, 156-159.

Chou. Y. H., Opal, P., Quinlan, R. A., and Goldman, R. D. (1996). The relative roles of specific N- and C-terminal phosphorylation sites in the disassembly of intermediate filament in mitotic BHK-21 cells. J. Cell Sci. 109, 817-826.

Chou. Y. H., Khuon, S., Hemmann, H., and Goldman, R. D. (2003). Nestin promotes the phosphorylation-dependent disassemble of vimentin intermediate filaments during mitosis. Mol. Biol. Cell. 14, 1468-1478.

Cory A H, Owen T C, Barltrop J A, Cory J G. (1991). Use of an aqueous soluble tetrazolium/formazan assay for cell growth assays in culture, Cancer Commun. 3, 207-212.

De Waegh, S. M., Lee, V. M., and Brady, S. T. (1992). Local modulation of neurofilament phosphorylation, axonal caliber, and slow axonal transport by myelinating Schwann cells. Cell 68, 451-463.

Eyer, J., and Leterrier, J. F. (1988). Influence of the phosphorylation state of neurofilament proteins on the in vitro interactions between purified filaments. Biochem. J. 252, 655-660.

Eyer, J., and Peterson, A. C. (1994). Neurofilament-deficient axons and perikaryal aggregates in viable transgenic mice expressing a neurofilament-beta-galactosidase fusion protein. Neuron 12, 389-405.

Fort, P., Marty, L., Piechaczyk, M., el Sabrouty, S., Dani, C., Jeanteur, P., and Blanchard, J. M. (1985). Various rat adult tissues express only one major mRNA species from the glyceraldehyde-3-phosphate-dehydrogenase multigenic family. Nucleic Acids Res. 13, 1431-1442.

Frank, R. (1992) Spot-Synthesis: An easy technique for the positionally addressable, parallel chemical synthesis on a membrane support. Tetrahedron 48, 9217-9232.

Frank, R. and Overwin, H. (1996) SPOT-Synthesis: Epitope analysis with arrays of synthetic peptides prepared on cellulose membranes. In: Methods in Molecular Biology, Vol. 66: Epitope Mapping Protocols (G. E. Monis, Ed.), The Humana Press Inc., Totowa, USA, 149-169.

Goto, H., Kosako, H., Tanabe, C., Yanagida; M., Sakurai, M., Amano, M., Kaibuchi, K., Inagaki, M. (199S) Phosphorylation of vimentin by Rho-associated kinase at a unique amino-terminal site that is specifically phosphorylated during cytokinesis. J. Biol. Chem. 273, 11728-11736.

Guillaud, L., Bosc, C., Fourest-Lieuvin, A., Denarier, E., Pirollet, F., Lafanechere, L., and Job, D. (1998). STOP proteins are responsible for the high degree of microtubule stabilization observed in neuronal cells. J. Cell Biol. 142, 167-179.

Hirokawa, N. (1982). Cross-linker system between neurofilaments, microtubules, and membranous organelles in frog axons revealed by the quick-freeze, deep-etching method. J. Cell Biol. 94, 129-142.

Hisanaga, S. and Hirokawa, N. (1990). Dephosphorylation-induced interactions of neurofilaments with microtubules. J. Biol. Chem. 265, 21852-21858.

Hoffman, P. N., and Cleveland, D. W., (1988). Neurofilament and tubulin expression recapitulates the developmental program during axonal regeneration: induction of a specific beta-tubulin isotype. Proc. Natl. Acad. Sci. USA. 85, 4530-4533.

Hoffman, P. N., Cleveland, D. W., Griffin, J. W., Landes, P. W., Cowan, N. J., and Price, D. L. (1987). Neurofilament gene expression: a major determinant of axonal caliber. Proc. Natl. Acad. Sci.-USA. 84, 3472-3476.

Julien, J. P., and Mushynski, W. E. (1982) Multiple phosphorylation sites in mammalian neurofilament polypeptides. J. Biol. Chem. 257, 10467-10470.

Ku, N. O., Liao, J., and Omary, M. B. (1998) Phosphorylation of human keratin 18 serine 33 regulates binding to 14-3-3 proteins. EMBO J. 17, 1892-1906.

Laemmli, U. K. (1970). Cleavage of structural proteins during the assembly of the head of bacteriophage T4. Nature 227, 680-685.

Lee, V. M. Y., Carden, M. J., Schlaepfer, W. W., Trojanowski, J. Q., Otvos, L., Hollosi, M., Dietzchold, B., Lazzarini, R. A. (1988). Identification of the major multiphosphorylation sites in mammalian neurofilaments. Proc. Natl. Acad. Sci.-USA 85, 1998-2002.

Mandelkow, E., and Mandelkow, E. M. (1995). Microtubules and microtubule-associated proteins. Curr. Opin. Cell Biol. 7, 72-81.

Ohara, O., Gahara, Y., Miyake, T., Teraoka, H., and Kitamura, T. (1993). Neurofilament deficiency in quail caused by nonsense mutation in neurofilament-L gene. J. Cell Biol. 121, 387-395.

Robert, P., Peterson, A., and Eyer, J. (2001). Neurofilament cytoskeleton does not modify accumulation of trophic factors mRNA. J. Neurosci. Res. 64, 487-492.

Toivola, D. M., Zhou, Q., English, L. S., and Omary, M. B. (2002) Type II keratins are phosphorylated on a unique motif during stress and mitosis in tissues and cultured cells. Mol. Biol. Cell 13, 1857-1870.

Weingarten, M. D., Lockwood, A. H., Hwo S.-Y., and Kirschner, M. W. (1975). A protein factor essential for microtubule assembly. Proc. Natl. Acad. Sci. USA. 72, 1858-1862.

Zhu, Q., Couillard-Despres, S., and Julien, J. P. (1997). Delayed maturation of regenerating myelinated axons in mice lacking neurofilaments. Exp. Neurol. 148, 299-316.

Zhu, Q., Lindenbaum, M., Levavasseur, F., Jacomy, H., and Julien, J. P. (1998). Disruption of the NFH gene increases axonal microtubule content and velocity of neurofilament transport: relief of axonopathy resulting from the toxin beta,beta'-iminodipropionitrile. J. Cell Biol. 143, 183-193.

The invention claimed is:

1. An isolated peptide consisting of a peptide of sequence with at least 92% of identity after optimum alignment with a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

2. The isolated peptide as claimed in 1, wherein said isolated peptide consists of a peptide of sequence with at least 95% of identity after optimum alignment with a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

3. The isolated peptide as claimed in 1, consisting of a peptide of a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

4. The isolated peptide as claimed in 1, wherein said peptide is synthesized by a recombinant technique or by chemical synthesis.

5. A method of production of recombinant peptide consisting of least 92% of identity after optimum alignment with a sequence selected from SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27, wherein said method comprises the following steps:
   a) culture of a cell transformed by a nucleic acid coding for said peptide or by a vector comprising said nucleic acid in a suitable culture medium in suitable culture conditions,
   b) recovery of said peptide from the cells or the culture medium obtained in step a).

6. The method as claimed in 5, wherein the recombinant peptide consists of at least 95% of identity after optimum alignment with a sequence selected from SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

7. The method as claimed in 6, wherein the recombinant peptide consists of a sequence selected from SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

8. A pharmaceutical composition comprising an isolated peptide consisting of a peptide of sequence with at least 92% of identity after optimum alignment with a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

9. The pharmaceutical composition as claimed in 8, wherein said isolated peptide consists of a peptide of sequence with at least 95% of identity after optimum alignment with a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

10. The pharmaceutical composition as claimed in 8, wherein said isolated peptide consists of a peptide of a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

11. A method for inhibiting cell proliferation and/or cell mobility comprising the administration to a subject of an isolated peptide consisting of a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

12. A method for detecting tubulin comprising the administration of an isolated peptide as a tubulin marker, wherein said isolated peptide consists of a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27.

13. A method for detecting and/or testing products that are able to block interaction between tubulin and an isolated peptide as a tubulin marker, wherein said isolated peptide consists of a sequence selected from the group consisting of SEQ ID NO: 5, SEQ ID NO: 6, SEQ ID NO: 7, SEQ ID NO: 8, SEQ ID NO: 17, SEQ ID NO: 18, SEQ ID NO: 20, SEQ ID NO: 21, SEQ ID NO: 23, SEQ ID NO: 26, and SEQ ID NO: 27, wherein said method comprises the step of incubating together tubulin, said isolated peptide and said product.

* * * * *

```
SEQUENCE LISTING

<160> NUMBER OF SEQ ID NOS: 52

<210> SEQ ID NO 1
<211> LENGTH: 72
<212> TYPE: DNA
<213> ORGANISM: Mus musculus

<400> SEQUENCE: 1
ttcggctacg atccgtactt ttcgacctcc tacaagcggc gctatgtgga dacgccccgg       60
gtgcacatct cc                                                          72

<210> SEQ ID NO 2
<211> LENGTH: 72
<212> TYPE: DNA
<213> ORGANISM: Mus musculus

<400> SEQUENCE: 2
actccgcgcc ggtctcctcc tcgctgtccg tgcgccgcag ctactcgtcc agctctggct       60
ctttgatgcc ca                                                          72

<210> SEQ ID NO 3
<211> LENGTH: 117
<212> TYPE: DNA
<213> ORGANISM: Mus musculus

<400> SEQUENCE: 3
gcctaccggc gcgttccaac cgagacccgg tccagcttca gccgcgtgag cggttccccg       60
```

```
tccagcggct tccgctcgca gtcctggtcc cgcggctcgc ccagcaccgt gtcctcc      117
```

<210> SEQ ID NO 4
<211> LENGTH: 117
<212> TYPE: DNA
<213> ORGANISM: Mus musculus

<400> SEQUENCE: 4

```
cgctccgcgg ccggctcctc cagcggcttc cactcgtggg cgcggacgtc cgtgagctcc      60
gtgtccgcct cacccagccg cttccgcggc gccgcctcga gcaccgactc gctagac        117
```

<210> SEQ ID NO 5
<211> LENGTH: 24
<212> TYPE: PRT
<213> ORGANISM: Mus musculus

<400> SEQUENCE: 5

Phe Gly Tyr Asp Pro Tyr Phe Ser Thr Ser Tyr Lys Arg Arg Tyr Val
 1               5                  10                  15

Glu Thr Pro Arg Val His Ile Ser
            20

<210> SEQ ID NO 6
<211> LENGTH: 24
<212> TYPE: PRT
<213> ORGANISM: Mus musculus

<400> SEQUENCE: 6

Tyr Ser Ser Tyr Ser Ala Pro Val Ser Ser Leu Ser Val Arg Arg
 1               5                  10                  15

Ser Tyr Ser Ser Ser Ser Gly Ser
            20

<210> SEQ ID NO 7
<211> LENGTH: 39
<212> TYPE: PRT
<213> ORGANISM: Mus musculus

<400> SEQUENCE: 7

Ala Tyr Arg Arg Val Pro Thr Glu Thr Arg Ser Ser Phe Ser Arg Val
 1               5                  10                  15

Ser Gly Ser Pro Ser Ser Gly Phe Arg Ser Gln Ser Trp Ser Arg Gly
            20                  25                  30

Ser Pro Ser Thr Val Ser Ser
        35

<210> SEQ ID NO 8
<211> LENGTH: 39
<212> TYPE: PRT
<213> ORGANISM: Mus musculus

<400> SEQUENCE: 8

Arg Ser Ala Ala Gly Ser Ser Gly Phe His Ser Trp Ala Arg Thr
 1               5                  10                  15

Ser Val Ser Val Ser Ala Ser Pro Ser Arg Phe Arg Gly Ala Ala
            20                  25                  30

Ser Ser Thr Asp Ser Leu Asp
        35

<210> SEQ ID NO 9

```
<211> LENGTH: 38
<212> TYPE: PRT
<213> ORGANISM: Mus musculus

<400> SEQUENCE: 9

Lys Ser Tyr Lys Met Ser Thr Ser Cys Pro Arg Ala Phe Ser Ser Arg
 1               5                  10                  15

Ser Phe Thr Ser Cys Pro Cys Ala Arg Ile Ser Ser Ser Pro Ser
                20                  25                  30

Arg Val Cys Ser Ser Ser
            35

<210> SEQ ID NO 10
<211> LENGTH: 38
<212> TYPE: PRT
<213> ORGANISM: Mus musculus

<400> SEQUENCE: 10

Lys Ser Tyr Lys Met Ser Thr Ser Cys Pro Arg Ala Phe Ser Ser Arg
 1               5                  10                  15

Ser Phe Thr Ser Cys Pro Cys Ala Arg Ile Ser Ser Ser Pro Ser
                20                  25                  30

Arg Val Cys Ser Ser Ser
            35

<210> SEQ ID NO 11
<211> LENGTH: 38
<212> TYPE: PRT
<213> ORGANISM: Mus musculus

<400> SEQUENCE: 11

Arg Phe Ser Ser Ser Arg Leu Leu Gly Ser Gly Ser Pro Ser Ser Ser
 1               5                  10                  15

Ala Arg Leu Gly Ser Phe Arg Ala Pro Arg Ala Gly Ala Leu Arg Leu
                20                  25                  30

Pro Ser Glu Arg Leu Asp
            35

<210> SEQ ID NO 12
<211> LENGTH: 27
<212> TYPE: PRT
<213> ORGANISM: Mus musculus

<400> SEQUENCE: 12

Met Ser Phe Gly Ser Glu His Tyr Leu Cys Ser Ala Ser Ser Tyr Arg
 1               5                  10                  15

Lys Val Phe Gly Asp Ser Ser Arg Leu Ser Ala
                20                  25

<210> SEQ ID NO 13
<211> LENGTH: 23
<212> TYPE: PRT
<213> ORGANISM: Mus musculus

<400> SEQUENCE: 13

Arg Gln Leu Gly Thr Met Pro Arg Phe Ser Leu Ser Arg Met Thr Pro
 1               5                  10                  15

Pro Leu Pro Ala Arg Val Asp
                20

<210> SEQ ID NO 14
```

```
<211> LENGTH: 41
<212> TYPE: PRT
<213> ORGANISM: Mus musculus

<400> SEQUENCE: 14

Arg Pro Ser Thr Ser Arg Ser Leu Tyr Ser Ser Pro Gly Gly Ala
 1               5                  10                  15

Tyr Val Thr Arg Ser Ser Ala Val Arg Leu Arg Ser Ser Val Pro Gly
            20                  25                  30

Val Arg Leu Leu Gln Asp Ser Val Asp
         35                  40

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgcaaggcg attaagttgg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gttgtgtgga attgtgagcg                                              20

<210> SEQ ID NO 17
<211> LENGTH: 27
<212> TYPE: PRT
<213> ORGANISM: Mus musculus

<400> SEQUENCE: 17

Met Ser Gln Ala Tyr Ser Ser Ser Gln Arg Val Ser Ser Tyr Arg Arg
 1               5                  10                  15

Thr Phe Gly Gly Ala Pro Gly Phe Ser Leu Gly
            20                  25

<210> SEQ ID NO 18
<211> LENGTH: 54
<212> TYPE: PRT
<213> ORGANISM: Mus musculus

<400> SEQUENCE: 18

Ser Ser Pro Val Phe Pro Arg Ala Gly Phe Gly Thr Lys Gly Ser Ser
 1               5                  10                  15

Ser Ser Met Thr Ser Arg Val Tyr Gln Val Ser Arg Thr Ser Gly Gly
            20                  25                  30

Ala Gly Gly Leu Gly Ser Leu Arg Ser Ser Arg Leu Gly Thr Thr Arg
         35                  40                  45

Ala Pro Ser Tyr Gly Ala
     50

<210> SEQ ID NO 19
<211> LENGTH: 21
<212> TYPE: PRT
```

<213> ORGANISM: Mus musculus

<400> SEQUENCE: 19

Gly Ser Glu Val His Thr Lys Lys Thr Val Met Ile Lys Thr Ile Glu
1               5                   10                  15
Thr Arg Asp Gly Glu
            20

<210> SEQ ID NO 20
<211> LENGTH: 18
<212> TYPE: PRT
<213> ORGANISM: Mus musculus

<400> SEQUENCE: 20

Met Ser Thr Arg Ser Val Ser Ser Ser Tyr Arg Arg Met Phe Gly
1               5                   10                  15
Gly Ser

<210> SEQ ID NO 21
<211> LENGTH: 24
<212> TYPE: PRT
<213> ORGANISM: Mus musculus

<400> SEQUENCE: 21

Gly Gly Ala Tyr Val Thr Arg Ser Ser Ala Val Arg Leu Arg Ser Ser
1               5                   10                  15
Val Pro Gly Val Arg Leu Leu Gln
            20

<210> SEQ ID NO 22
<211> LENGTH: 21
<212> TYPE: PRT
<213> ORGANISM: Mus musculus

<400> SEQUENCE: 22

Ser Leu Pro Leu Val Asp Thr His Ser Lys Arg Thr Leu Leu Ile Lys
1               5                   10                  15
Thr Val Glu Thr Arg
            20

<210> SEQ ID NO 23
<211> LENGTH: 54
<212> TYPE: PRT
<213> ORGANISM: Mus musculus

<400> SEQUENCE: 23

Met Ser Ile Arg Val Thr Gln Lys Ser Tyr Lys Met Ser Thr Ser Gly
1               5                   10                  15
Pro Arg Ala Phe Ser Ser Arg Ser Phe Thr Ser Gly Pro Gly Ala Arg
            20                  25                  30
Ile Ser Ser Ser Ser Phe Ser Arg Val Gly Ser Ser Ser Ser Phe
        35                  40                  45
Arg Gly Ser Met Gly Thr
    50

<210> SEQ ID NO 24
<211> LENGTH: 21
<212> TYPE: PRT
<213> ORGANISM: Mus musculus

<400> SEQUENCE: 24

Gln Ile Lys Ser Leu Asn Asn Lys Phe Ala Ser Phe Ile Asp Lys Val
1               5                   10                  15

Arg Phe Leu Glu Gln
            20

<210> SEQ ID NO 25
<211> LENGTH: 30
<212> TYPE: PRT
<213> ORGANISM: Mus musculus

<400> SEQUENCE: 25

Ser Ala Gly Gly Ser Asn Thr Phe Ser Arg Thr Thr Lys Ala Val Val
1               5                   10                  15

Val Lys Lys Ile Glu Thr Arg Asp Gly Lys Leu Val Ser Glu
            20                  25                  30

<210> SEQ ID NO 26
<211> LENGTH: 24
<212> TYPE: PRT
<213> ORGANISM: Mus musculus

<400> SEQUENCE: 26

Met Glu Arg Arg Arg Ile Thr Ser Ala Arg Arg Ser Tyr Ala Ser Glu
1               5                   10                  15

Thr Val Val Arg Gly Leu Gly Pro
            20

<210> SEQ ID NO 27
<211> LENGTH: 36
<212> TYPE: PRT
<213> ORGANISM: Mus musculus

<400> SEQUENCE: 27

Val Arg Gly Leu Gly Pro Ser Arg Gln Leu Gly Thr Met Pro Arg Phe
1               5                   10                  15

Ser Leu Ser Arg Met Thr Pro Pro Leu Pro Ala Arg Val Asp Phe Ser
            20                  25                  30

Leu Ala Gly Ala
        35

<210> SEQ ID NO 28
<211> LENGTH: 21
<212> TYPE: PRT
<213> ORGANISM: Mus musculus

<400> SEQUENCE: 28

Lys Ser Val Ser Glu Gly His Leu Lys Arg Asn Ile Val Val Lys Thr
1               5                   10                  15

Val Glu Met Arg Asp
            20

<210> SEQ ID NO 29
<211> LENGTH: 81
<212> TYPE: DNA
<213> ORGANISM: Mus musculus

<400> SEQUENCE: 29
atgagccagg cctactcgtc cagccagcgc gtgtcctcct accgccgcac cttcggcggc    60
gccccgggct tctctctggg c                                              81

<210> SEQ ID NO 30

<211> LENGTH: 166
<212> TYPE: DNA
<213> ORGANISM: Mus musculus

<400> SEQUENCE: 30

```
gagctctccc gtgttccctc gagcaggctt cggtaccaag ggctcctcga gttcaatgac    60
atcccgcgtg taccaggtgt cgcgcacgtc gggcggggct ggaggcttgg ggtcgctgcg   120
gtctagccgg ctggggacca cccgagcgcc atcctatggc gcgggc                 166
```

<210> SEQ ID NO 31
<211> LENGTH: 61
<212> TYPE: DNA
<213> ORGANISM: Mus musculus

<400> SEQUENCE: 31

```
ttctgaagtc cataccaaaa agacagtgat gatcaagacc attgagaccc gggatggaga    60
g                                                                   61
```

<210> SEQ ID NO 32
<211> LENGTH: 54
<212> TYPE: DNA
<213> ORGANISM: Mus musculus

<400> SEQUENCE: 32

```
atgtctacca ggtctgtgtc ctcgtcctcc taccgcagga tgttcggtgg ctcc          54
```

<210> SEQ ID NO 33
<211> LENGTH: 73
<212> TYPE: DNA
<213> ORGANISM: Mus musculus

<400> SEQUENCE: 33

```
cggtggcgcc tatgtgaccc ggtcctcggc agtgcgcctg cggagcagcg tgccgggcgt    60
gcggctgctt caa                                                      73
```

<210> SEQ ID NO 34
<211> LENGTH: 60
<212> TYPE: DNA
<213> ORGANISM: Mus musculus

<400> SEQUENCE: 34

```
cttcctctgg ttgacaccca ctcaaaaaga acactcctga ttaagacggt tgagaccaga    60
```

<210> SEQ ID NO 35
<211> LENGTH: 161
<212> TYPE: DNA
<213> ORGANISM: Mus musculus

<400> SEQUENCE: 35

```
tgtccatcag ggtgactcag aaatcctaca agatgtccac ctccggtccc cgggccttca    60
gcagccgctc gttcacgagt ggaccccgtg cccgcatcag ctcttccagc ttttcccggg   120
tgggcagcag cagcagcagc ttccggggaa gcatgggcac c                       161
```

<210> SEQ ID NO 36
<211> LENGTH: 61
<212> TYPE: DNA
<213> ORGANISM: Mus musculus

<400> SEQUENCE: 36

```
gattaaatcc ctgaacaaca agttcgcctc cttcattgac aaggtgcgct tcctggagca    60
```

```
<210> SEQ ID NO 37
<211> LENGTH: 88
<212> TYPE: DNA
<213> ORGANISM: Mus musculus

<400> SEQUENCE: 37
tgccggggga tccaacactt tcagccgcac caccaaggct gtggttgtga agaagattga    60
aacccgagat gggaagctgg tgtccgag                                      88

<210> SEQ ID NO 38
<211> LENGTH: 72
<212> TYPE: DNA
<213> ORGANISM: Mus musculus

<400> SEQUENCE: 38
atgcctccga cggtggtc agggcctct ggtcctagtc gacaactggg taccatgcca      60
cgtttctcct tg                                                        72

<210> SEQ ID NO 39
<211> LENGTH: 106
<212> TYPE: DNA
<213> ORGANISM: Mus musculus

<400> SEQUENCE: 39
gccacgtttc tccttgtctc gaatgactcc tccactccct gccagggtgg acttctccct    60
ggccggggcg ctcaatgctg gcttcaagga gacacgggcg agcgag                  106

<210> SEQ ID NO 40
<211> LENGTH: 61
<212> TYPE: DNA
<213> ORGANISM: Mus musculus

<400> SEQUENCE: 40
ggtaaagact gtggagatgc gggatggtga ggtcattaag gactcgaagc aggagcacaa    60
g                                                                    61

<210> SEQ ID NO 41
<211> LENGTH: 72
<212> TYPE: PRT
<213> ORGANISM: Mus musculus

<400> SEQUENCE: 41

Met Ser Ser Phe Gly Tyr Asp Pro Tyr Phe Ser Thr Ser Tyr Lys Arg
  1               5                  10                  15

Arg Tyr Val Glu Thr Pro Arg Val His Ile Ser Ser Val Arg Ser Gly
                 20                  25                  30

Tyr Ser Thr Ala Arg Ser Ala Tyr Ser Ser Tyr Ser Ala Pro Val Ser
             35                  40                  45

Ser Ser Leu Ser Val Arg Arg Ser Tyr Ser Ser Ser Gly Ser Leu
     50                  55                  60

Met Pro Ser Leu Glu Asn Leu Asp
 65                  70

<210> SEQ ID NO 42
<211> LENGTH: 77
<212> TYPE: PRT
<213> ORGANISM: Mus musculus
```

-continued

<400> SEQUENCE: 42

Met Ser Tyr Thr Leu Asp Ser Leu Gly Asn Pro Ser Ala Tyr Arg Arg
1               5                   10                  15

Val Pro Thr Glu Thr Arg Ser Ser Phe Ser Arg Val Ser Gly Ser Pro
            20                  25                  30

Ser Ser Gly Phe Arg Ser Gln Ser Trp Ser Arg Gly Ser Pro Ser Thr
        35                  40                  45

Val Ser Ser Ser Tyr Thr Arg Ser Ala Val Ala Pro Arg Leu Ala Tyr
    50                  55                  60

Ser Ser Ala Met Leu Ser Ser Ala Glu Ser Ser Leu Asp
65                  70                  75

<210> SEQ ID NO 43
<211> LENGTH: 75
<212> TYPE: PRT
<213> ORGANISM: Mus musculus

<400> SEQUENCE: 43

Met Ser Phe Gly Ser Ala Asp Ala Leu Leu Gly Ala Pro Phe Ala Pro
1               5                   10                  15

Leu His Gly Gly Gly Ser Leu His Tyr Ser Leu Ser Arg Lys Ala Gly
            20                  25                  30

Pro Gly Gly Thr Arg Ser Ala Ala Gly Ser Ser Ser Gly Phe His Ser
        35                  40                  45

Trp Ala Arg Thr Ser Val Ser Ser Val Ser Ala Ser Pro Ser Arg Phe
    50                  55                  60

Arg Gly Ala Ala Ser Ser Thr Asp Ser Leu Asp
65                  70                  75

<210> SEQ ID NO 44
<211> LENGTH: 74
<212> TYPE: PRT
<213> ORGANISM: Mus musculus

<400> SEQUENCE: 44

Met Ser Ser Phe Gly Tyr Asp Pro Tyr Phe Ser Thr Ser Tyr Lys Arg
1               5                   10                  15

Arg Tyr Val Glu Thr Pro Arg Val His Ile Ser Ser Val Arg Ser Gly
            20                  25                  30

Tyr Ser Thr Ala Arg Ser Ala Tyr Ser Ser Tyr Ser Ala Pro Val Ser
        35                  40                  45

Ser Ser Leu Ser Val Arg Arg Ser Tyr Ser Ser Ser Gly Ser Leu
    50                  55                  60

Met Pro Ser Leu Glu Asn Leu Asp Val Ser
65                  70

<210> SEQ ID NO 45
<211> LENGTH: 79
<212> TYPE: PRT
<213> ORGANISM: Mus musculus

<400> SEQUENCE: 45

Met Ser Tyr Thr Leu Asp Ser Leu Gly Asn Pro Ser Ala Tyr Arg Arg
1               5                   10                  15

Val Pro Thr Glu Thr Arg Ser Ser Phe Ser Arg Val Ser Gly Ser Pro
            20                  25                  30

Ser Ser Gly Phe Arg Ser Gln Ser Trp Ser Arg Gly Ser Pro Ser Thr

```
                       35                  40                  45
Val Ser Ser Ser Tyr Thr Arg Ser Ala Val Ala Pro Arg Leu Ala Tyr
         50                  55                  60

Ser Ser Ala Met Leu Ser Ser Ala Glu Ser Ser Leu Asp Phe Ser
 65                  70                  75
```

<210> SEQ ID NO 46
<211> LENGTH: 78
<212> TYPE: PRT
<213> ORGANISM: Mus musculus

<400> SEQUENCE: 46

```
Met Ser Phe Gly Ser Ala Asp Ala Leu Leu Gly Ala Pro Phe Ala Pro
  1               5                  10                  15

Leu His Gly Gly Gly Ser Leu His Tyr Ser Leu Ser Arg Lys Ala Gly
                 20                  25                  30

Pro Gly Gly Thr Arg Ser Ala Ala Gly Ser Ser Ser Gly Phe His Ser
             35                  40                  45

Trp Ala Arg Thr Ser Val Ser Val Ser Ala Ser Pro Ser Arg Phe
 50                  55                  60

Arg Gly Ala Ala Ser Ser Thr Asp Ser Leu Asp Thr Leu Ser
 65                  70                  75
```

<210> SEQ ID NO 47
<211> LENGTH: 91
<212> TYPE: PRT
<213> ORGANISM: Mus musculus

<400> SEQUENCE: 47

```
Met Ser Gln Ala Tyr Ser Ser Ser Gln Arg Val Ser Ser Tyr Arg Arg
  1               5                  10                  15

Thr Phe Gly Gly Ala Pro Gly Phe Ser Leu Gly Ser Pro Leu Ser Ser
                 20                  25                  30

Pro Val Phe Pro Arg Ala Gly Phe Gly Thr Lys Gly Ser Ser Ser Ser
             35                  40                  45

Met Thr Ser Arg Val Tyr Gln Val Ser Arg Thr Ser Gly Gly Ala Gly
 50                  55                  60

Gly Leu Gly Ser Leu Arg Ser Ser Arg Leu Gly Thr Thr Arg Ala Pro
 65                  70                  75                  80

Ser Tyr Gly Ala Gly Glu Leu Leu Asp Phe Ser
                 85                  90
```

<210> SEQ ID NO 48
<211> LENGTH: 87
<212> TYPE: PRT
<213> ORGANISM: Mus musculus

<400> SEQUENCE: 48

```
Met Ser Thr Arg Ser Val Ser Ser Ser Tyr Arg Arg Met Phe Gly
  1               5                  10                  15

Gly Ser Gly Thr Ser Ser Arg Pro Ser Ser Asn Arg Ser Tyr Val Thr
                 20                  25                  30

Thr Ser Thr Arg Thr Tyr Ser Leu Gly Ser Ala Leu Arg Pro Ser Thr
             35                  40                  45

Ser Arg Ser Leu Tyr Ser Ser Ser Pro Gly Gly Ala Tyr Val Thr Arg
 50                  55                  60

Ser Ser Ala Val Arg Leu Arg Ser Ser Val Pro Gly Val Arg Leu Leu
 65                  70                  75                  80
```

```
<210> SEQ ID NO 49
<211> LENGTH: 81
<212> TYPE: PRT
<213> ORGANISM: Mus musculus

<400> SEQUENCE: 49

Met Ser Ile Arg Val Thr Gln Lys Ser Tyr Lys Met Ser Thr Ser Gly
 1               5                  10                  15

Pro Arg Ala Phe Ser Ser Arg Ser Phe Thr Ser Gly Pro Gly Ala Arg
             20                  25                  30

Ile Ser Ser Ser Phe Ser Arg Val Gly Ser Ser Ser Ser Ser Ser Phe
         35                  40                  45

Arg Gly Ser Met Gly Thr Gly Val Gly Leu Gly Phe Gly Gly Ala
     50                  55                  60

Gly Val Gly Gly Ile Thr Ala Val Thr Val Asn Gln Ser Leu Leu Ser
 65                  70                  75                  80

Pro

<210> SEQ ID NO 50
<211> LENGTH: 50
<212> TYPE: PRT
<213> ORGANISM: Mus musculus

<400> SEQUENCE: 50

Met Glu Arg Arg Arg Ile Thr Ser Ala Lys Arg Ser Tyr Ala Ser Glu
 1               5                  10                  15

Thr Val Val Arg Gly Leu Gly Pro Ser Arg Gln Leu Gly Thr Met Pro
             20                  25                  30

Arg Phe Ser Leu Ser Arg Met Thr Pro Pro Leu Pro Ala Arg Val Asp
         35                  40                  45

Phe Ser
     50

<210> SEQ ID NO 51
<211> LENGTH: 85
<212> TYPE: PRT
<213> ORGANISM: Mus musculus

<400> SEQUENCE: 51

Met Pro Ser Ser Ala Ser Met Ser His His Ser Ser Gly Leu Arg
 1               5                  10                  15

Ser Ser Ile Ser Ser Thr Ser Tyr Arg Arg Thr Phe Gly Pro Pro
             20                  25                  30

Ser Leu Ser Pro Gly Ala Phe Ser Tyr Ser Ser Ser Arg Phe Ser
         35                  40                  45

Ser Ser Arg Leu Leu Gly Ser Gly Ser Pro Ser Ser Ala Arg Leu
     50                  55                  60

Gly Ser Phe Arg Ala Pro Arg Ala Gly Ala Leu Arg Leu Pro Ser Glu
 65                  70                  75                  80

Arg Leu Asp Phe Ser
             85

<210> SEQ ID NO 52
<211> LENGTH: 78
<212> TYPE: PRT
```

-continued

```
<213> ORGANISM: Mus musculus

<400> SEQUENCE: 52

Met Ser Phe Gly Ser Glu His Tyr Leu Cys Ser Ala Ser Ser Tyr Arg
 1               5                  10                  15

Lys Val Phe Gly Asp Ser Ser Arg Leu Ser Ala Arg Leu Ser Gly Pro
            20                  25                  30

Gly Gly Ser Gly Ser Phe Arg Ser Gln Ser Leu Ser Arg Ser Asn Val
         35                  40                  45

Ala Ser Thr Ala Ala Cys Ser Ser Ala Ser Ser Leu Gly Leu Gly Leu
     50                  55                  60

Ala Tyr Arg Arg Leu Pro Ala Ser Asp Gly Leu Asp Leu Ser
 65                  70                  75
```